US011672772B2

(12) United States Patent
Zhang

(10) Patent No.: US 11,672,772 B2
(45) Date of Patent: Jun. 13, 2023

(54) USE OF GLYCYRRHETINIC ACID, GLYCYRRHIZIC ACID AND RELATED COMPOUNDS FOR MITIGATION AND/OR TREATMENT OF PNEUMONITIS/PNEUMONIA/PULMONARY FIBROSIS INDUCED BY VIRUS INFECTION AND/OR BY CHEMICAL OR BIOLOGICAL AGENTS

(71) Applicant: Lurong Zhang, Bethesda, MD (US)

(72) Inventor: Lurong Zhang, Bethesda, MD (US)

( * ) Notice: Subject to any disclaimer, the term of this patent is extended or adjusted under 35 U.S.C. 154(b) by 75 days.

(21) Appl. No.: 17/170,388

(22) Filed: Feb. 8, 2021

(65) Prior Publication Data

US 2021/0244691 A1    Aug. 12, 2021

Related U.S. Application Data

(60) Provisional application No. 62/971,921, filed on Feb. 8, 2020.

(51) Int. Cl.
*A61K 31/19* (2006.01)
*A61K 31/14* (2006.01)
*A61K 31/704* (2006.01)
*A61P 31/14* (2006.01)

(52) U.S. Cl.
CPC ............ *A61K 31/19* (2013.01); *A61K 31/704* (2013.01); *A61P 31/14* (2018.01)

(58) Field of Classification Search
None
See application file for complete search history.

(56) References Cited

U.S. PATENT DOCUMENTS 9,416,151 B2 * 8/2016 Zhang ..................... A61P 29/00

FOREIGN PATENT DOCUMENTS

| CN | 101919870 B | 3/2013 |
| JP | H10330256 A | 12/1998 |
| WO | 2012026928 A1 | 3/2012 |

OTHER PUBLICATIONS

Hoever, G. et al. "Antiviral activity of glycyrrhizic acid derivatives against SARS-coronavirus." Journal of medicinal chemistry, 2005, 48: 1256-1259.
Alcon, A., et al., "Hospital-acquired pneumonia: etiologic considerations." Infect Dis Clin N Am, 2003, 17: Abstract.
American Thoracic Society Documents, "Guidelines for the Management of Adults with Hospital-acquired, Ventilator-associated, and Healthcare-associated Pneumonia" Am J Respoir Crit Care Med, 2005, 171: 388-416.
Amratia, D.A., et al., "Glucocorticoid therapy in respiratory illness: bench to bedside." J Investig Med, 2022, 70: 1662-1680.
Armanini, D., et al. ,"Affinity of Liquorice Derivatives for Mineralocorticoid and Glucocorticoid Receptors." Clinical Endocrinology, 1983, 19(5): Abstract.
Avecillas, J.F., et al., "A rational approach to the evaluation and treatment of the infected patient in the intensive care unit." Clinics in Chest Medicine, Dec. 2003, 24(4): Abstract.
Evans, S.E., et al., "Pneumonia in the neutropenic cancer patient." Curr Opin Pulm Med., 2015, 21(3): 260-271.
Feng, J., et al., "Rapid On-Site Evaluation (ROSE) in Diagnostic Interventional Pulmonology, Volume 1: Infections Diseases." Springer Singapore, 2019, <<https://doi.org/10.1007/978-981-13-3456-6>>, Abstract.
Handa, S., et al., "Effect of intravenous pulse dexamethoasone versus daily oral prednisolone on bone mineral density in dermatology patients: Is it a site-specific response?" Indian Journal of Dermatology, Venerology and Leprology, 2018, 84(2): 174-178.
Harris, E., et al., "The Prediction and Monitoring of Toxicity Associated with Long-Term Systemic Glucocorticoid Therapy." Current Rheumatology Reports, 2018, 17(38): Abstract.
He, Y., et al., "Antagonistic effect of compound glycyrrhizin on bleomycin-induced pulmonary fibrosis of rats." China Pharmacy, 2008, 17(7): Abstract.
Kao, T.-C., et al., "Glycyrrhizic Acid and 18β-Glycyrrhetinic Acid Inhibit Inflammation via PI3K/Akt/GSK3β Signaling and Glucocorticoid Receptor Activation." J. Agric. Food Chem., 2010, 58(15): Abstract.
Lyall, M.J., et al., "Diurnal profile of interstitial glucose following dexamethasone prophylaxis for chemotherapy treatment of gynaecological cancer." Diabetic Medicine, 2018, 35(11): Abstract.
Niederman, M.S., "Severe Pneumonia." Shock, 2006, 25(1): 94-95.
Pisani, M., "Aging and Lung Disease: A Clinical Guide (Respiratory Medicine)." Humana, 2012, Abstract.
Seitz, T., et al., "The Role of Bacterial and Fungal Superinfection in Critical COVID-19." Viruses, 2022, 14(2785): 1-12.
Siso-Almirall, A., et al., "Long Covid-19: Proposed Primary Care Clinical Guidelines for Diagnosis and Disease Management." International Journal of Environmental Research and Public Health, 2021, 18(4350): 1-20.
Taniguchi, H., et al., "Acute and subacute idiopathic interstitial pneumonias." Respirology, 2016, 21: 810-820.
Ulmann, A., et al., "Binding of Glycyrrhetinic Acid to Kidney Mineralocorticoid and Glucocorticoid Receptors." Endocrinology, Jul. 1975, 97(1): Abstract.
Villadsen, L.T., "Interstitial Lung Disease: Causes, Diagnosis and Treatment." Nova Science Publishers, Inc., 2019, Abstract.

(Continued)

*Primary Examiner* — Traviss C McIntosh, III
(74) *Attorney, Agent, or Firm* — Saliwanchik, Lloyd & Eisenschenk

(57) ABSTRACT

The present invention pertains to novel uses of glycyrrhetinic acid (GA), glycyrrhizic acid (GR) and related compounds for mitigation and/or treatment of pneumonitis/pneumonia/pulmonary fibrosis induced by various chemicals/bioagents and/or pathogens, such as anti-cancer therapies and/or virus.

Also embodied are therapeutic uses of prodrugs, metabolites, derivatives (e.g., acids, esters and ethers), and salts of glycyrrhetinic acid (GA) and glycyrrhizic acid (GR) in a form of drugs, health products, foods or food additives.

9 Claims, 23 Drawing Sheets

(56) References Cited

OTHER PUBLICATIONS

Vogel, F., et al., "Endocrine risk factors for COVID-19: Endogenous and exogenous glucocorticoid excess." Reviews in Endocrine and Metabolic Disorders, 2022, 23:233-250.

Wang, Y.-X., "Lung Inflammation in Health and Disease, vol. II" Springer Nature, 2021, 1304: Abstract.

Wang, X., et al., "Experimental Study on Effect of Stronger NEO—Minophagen C in Treating Rats with Belomycin-induced Pulmonary Fibrosis." Chinese Archives of Traditional Chinese Medicine, Dec. 2008, 26(12): Abstract.

* cited by examiner

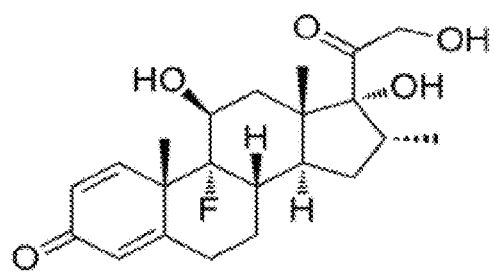
Dexamethasone
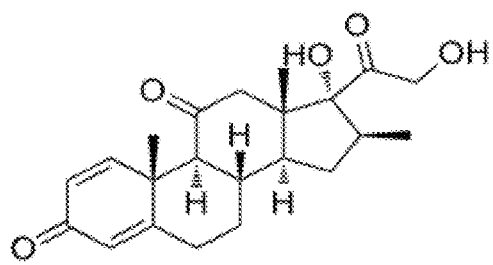
Methylprednisone
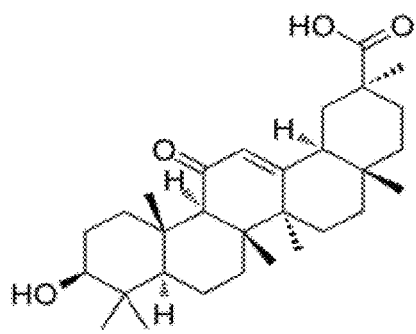
Glycyrrhetinic acid (GA, aglycone, liposoluble, intracellular)
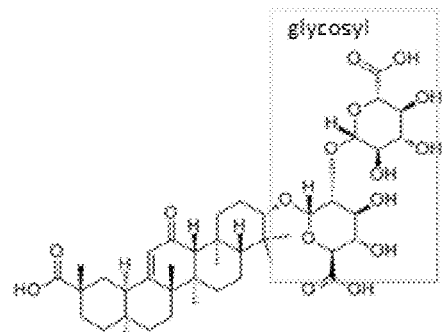
Glycyrrhizic acid (GR, water-soluble, entering cells after removing glycosyl)
FIG. 1

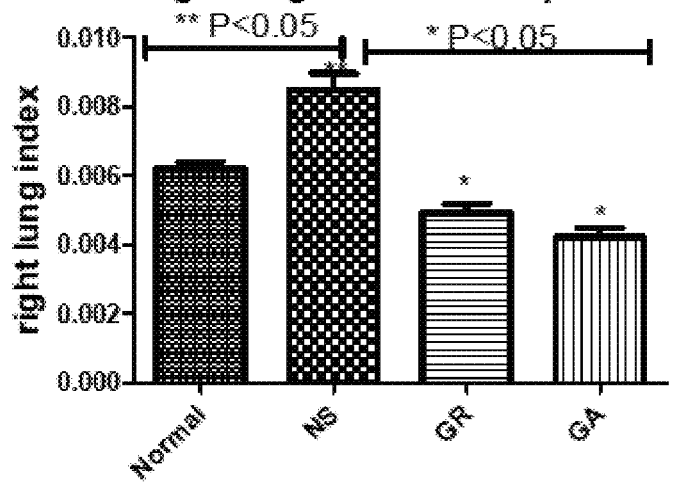
FIG. 3B

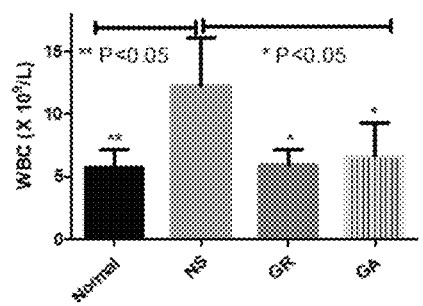
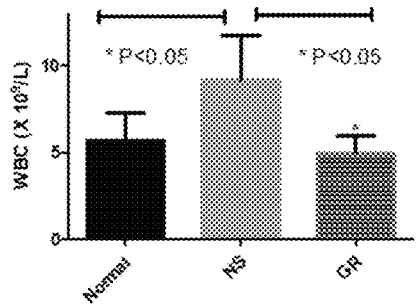
FIG. 9A                FIG. 9B
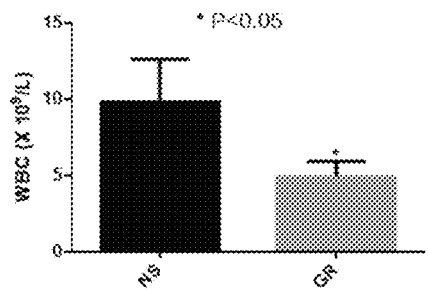
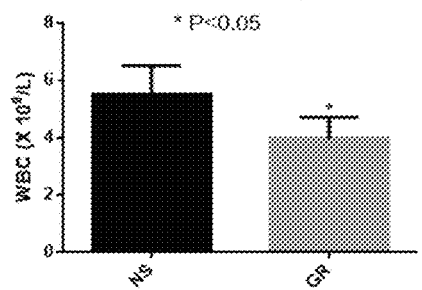
FIG. 9C                FIG. 9D
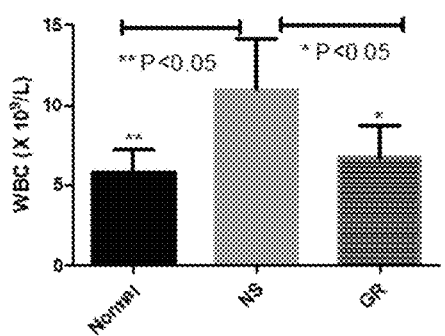
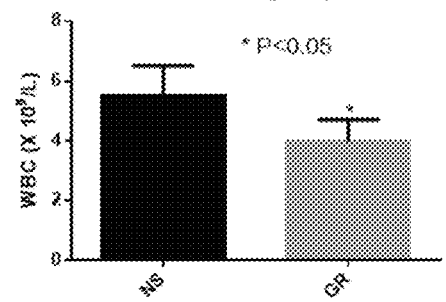
FIG. 9E                FIG. 9F

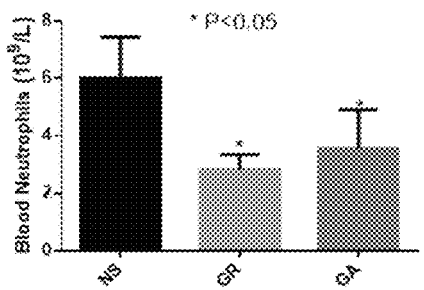
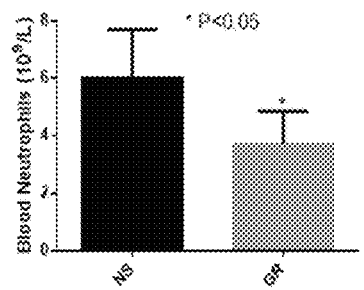
FIG. 13C
FIG. 13D
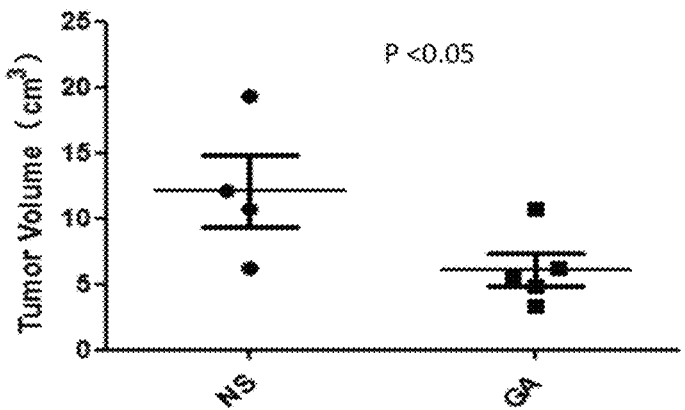
FIG. 14
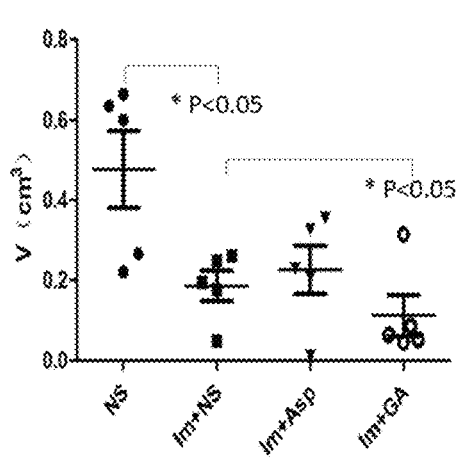
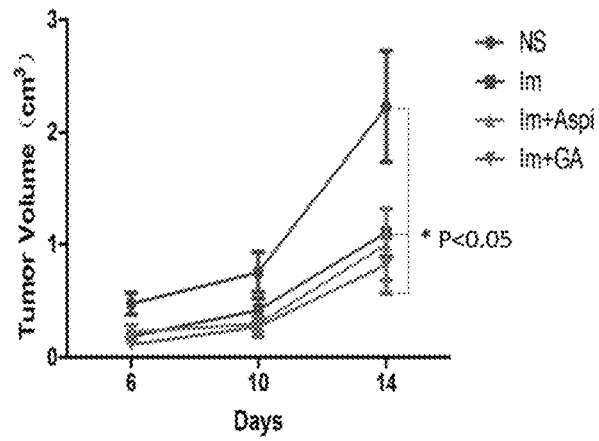
FIG. 15A
FIG. 15B

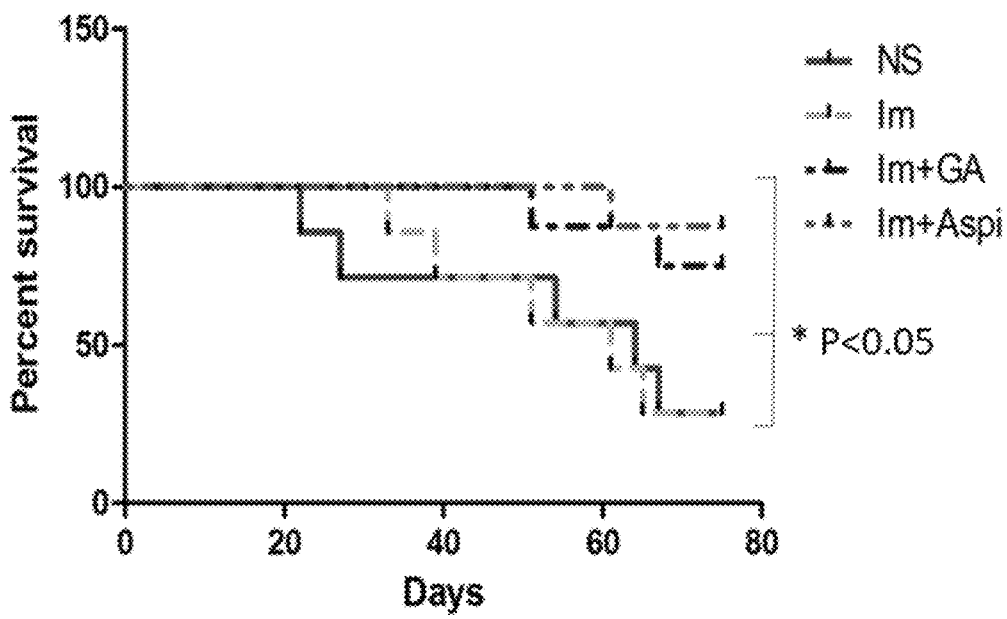

FIG. 16

GR reduces Osimertinib-induced pneumonitis in patient with lung cancer

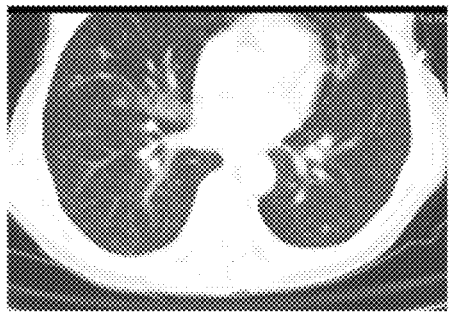

Mild pneumonitis occured after one month treated with Osimertinib (80 mg/day) to target EGFR pathway.

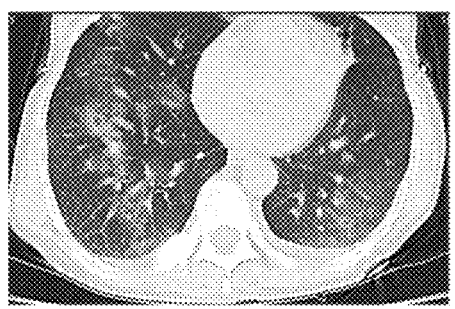

Moderate pneumonitis existed after two months treated with Osimertinib. GR was orally started to treat pneumonitis.

One month after using GR, pneumonitis was reduced while Osimertinib was used continuously to target EGFR pathway.

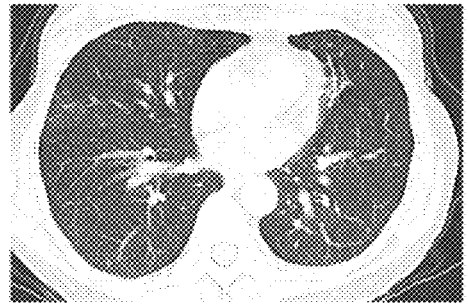

Six months after using GR, pneumonitis subsided while Osimertinib was used continuously to target EGFR pathway.

FIG. 17

Automatic segmentation analysis for alterations of CT density with lesion

Step 1: Adjust the window width and level to the lung at the similar anatomic position*

*: When CT is taken, the body position, CT parameters and operator must be consistent to ensure the similar anatomic position.

The followings are the steps to determine the density in each CT

Step 2: Otsu threshold segmentation is used to determine the lung contour

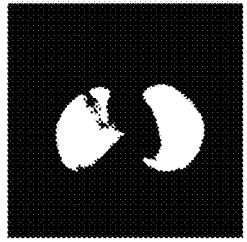

Fig 2

Step 3: FCM clustering is used to cluster the lung into two groups (Fig. 3) and automatically determine the inflammation (Fig. 4), because it will aggregate the blood vessels into inflammation. Therefore, the next step is to delete the vessel.

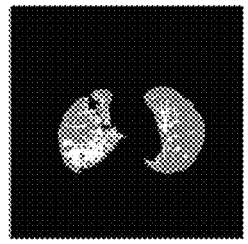
Fig. 3

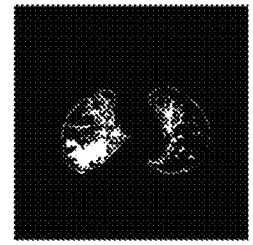
Fig. 4

FIG. 21C

Step 4: To judge if the inflammation destroys the lung contour (observed manually), if so, the rolling ball method is used to repair the contour (Fig. 5).

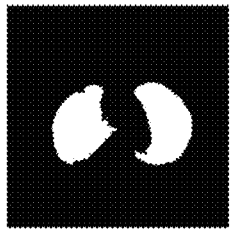
Fig. 5

Step 5: The inflammation image (Fig 4) automatically found in the third step is used for opening operation (first corrosion and then expansion). Since there are many small noises and blood vessels, which are relatively slender, by using the open operation (Fig 6), these slender parts can be deleted, and the inflammatory part in ball can be basically retained.

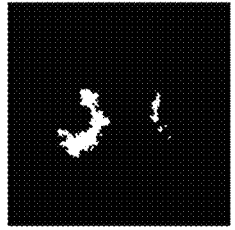
Fig 6

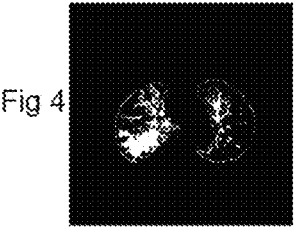
Fig 4

FIG. 21D

Step 6: For convenience of comparison, put Fig. 4 and Fig. 6 together, take out the position marked in Fig. 6 at the position marked in Fig. 4, the post-processing method is to delete the slender part by Euclidean distance transformation. The final result is shown in Fig. 7

Defferent densities between two sets of CT from Patient 1

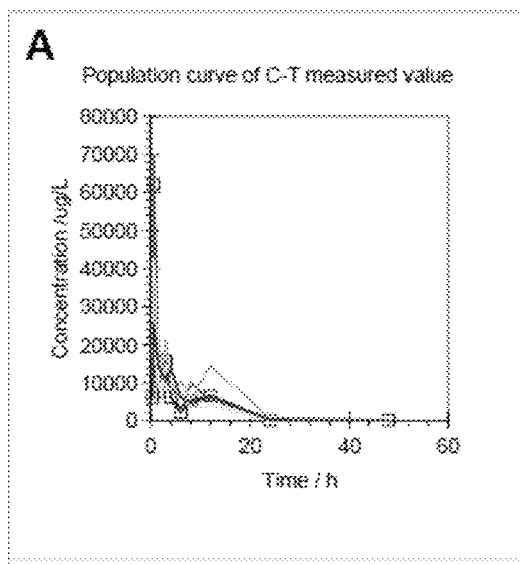
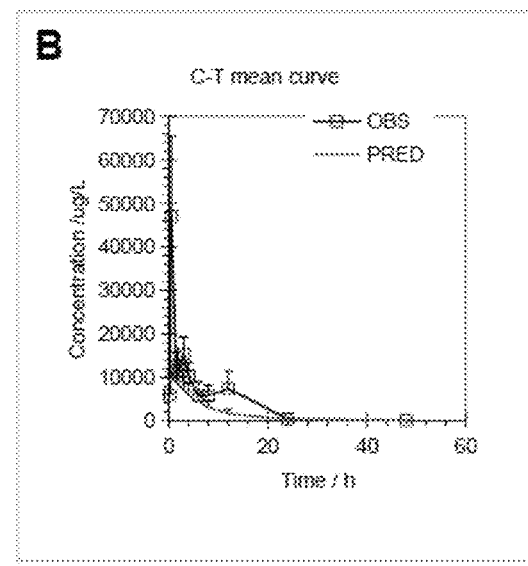
FIG. 22A  FIG. 22B
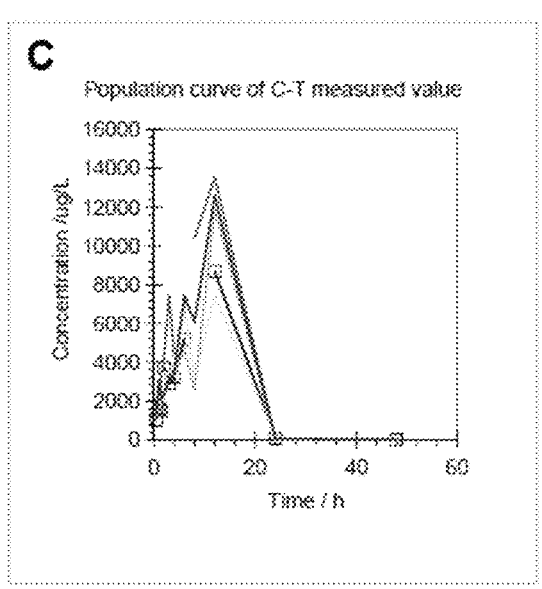
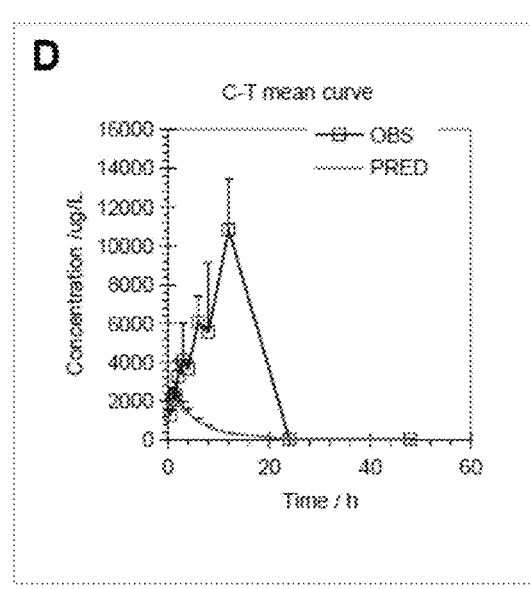
FIG. 22C  FIG. 22D

The differences in pharmacokinetics between GR and GA

| Parameter | Unit | GA Mean | GR Mean |
|---|---|---|---|
| AUC(0-t) | ug/L*h | 172682.554 | 132693.352 |
| AUC(0-∞) | ug/L*h | 172886.951 | 133034.212 |
| R_AUC(t/∞) | % | 99.88 | 99.78 |
| AUMC(0-t) | h*h*ug/L | 1204903.821 | 1346031.773 |
| AUMC(0-∞) | h*h*ug/L | 1216221.888 | 1365014.153 |
| MRT(0-t) | h | 6.744 | 10.123 |
| MRT(0-∞) | h | 6.806 | 10.239 |
| VRT(0-t) | h^2 | 30.872 | 17.312 |
| VRT(0-∞) | h^2 | 33.933 | 22.681 |
| $\lambda z$ | 1/h | 0.149 | 0.135 |
| C_last | ug/L | 27.932 | 44.553 |
| t1/2z | h | 4.782 | 5.179 |
| Tmax | h | 0.5 | 12 |
| Vz/F | L/kg | 9.74 | 23.49 |
| CLz/F | L/h/kg | 1.382 | 3.133 |
| Cmax | ug/L | 47076.716 | 10842.175 |

FIG. 23

USE OF GLYCYRRHETINIC ACID, GLYCYRRHIZIC ACID AND RELATED COMPOUNDS FOR MITIGATION AND/OR TREATMENT OF PNEUMONITIS/PNEUMONIA/PULMONARY FIBROSIS INDUCED BY VIRUS INFECTION AND/OR BY CHEMICAL OR BIOLOGICAL AGENTS

CROSS-REFERENCE TO A RELATED APPLICATION

This application claims the priority benefit of U.S. Provisional Application Ser. No. 62/971,921, filed Feb. 8, 2020, which is incorporate herein by reference in its entirety.

TECHNICAL FIELD

The invention relates generally to uses of glycyrrhetinic acid, glycyrrhizic acid and related compounds for mitigation and/or treatment of pneumonitis/pneumonia/pulmonary fibrosis induced by virus infection and/or by chemical or biological agents.

BACKGROUND OF THE INVENTION

Pneumonitis/pneumonia/pulmonary fibrosis is a serious life-threatening disease caused by various factors, such as anti-cancer drugs, chemicals, virus, radiation, biological compounds which damage the DNA/proteins or trigger the host reactions against the invading harmful factors.

The symptoms of pneumonitis/pneumonia may include cough, shortness of breath, chest tightness, weakness, fever, and severe respiratory distress. Pathologically, there is an increased exudation, thickened interstitial and lung densification. CT images can show the multiple small plaque shadows or ground-GRss shadows in lungs. In the severe cases, lung consolidation may occur. Blood tests show that the total number of white blood cells and neutrophils can be surged. Biochemically, there can be a series of stress reactions, such as increased various cytokines and chemokines, C-reaction protein, erythrocyte sedimentation rate/procalcitonin, liver enzymes, myoenzymes, myoglobin and etc.

If the etiological factors persist, there can be a transition from pneumonitis/pneumonia into pulmonary fibrosis, which is much more difficult to treat and greatly affects the quality of life.

While the use of targeted/immune therapies for anticancer has achieved exciting effects, more and more side-effects are found.

Glucocorticoids have been used to treat severe pneumonitis/pneumonia. For example, it was used in the treatment of SARS (severe acute respiratory syndrome) in 2003. However, its strong side effects (cortex hyperactivity syndrome, infection, ulcer disease, osteoporosis, etc.) make the survivors of SARS suffering from femoral head necrosis and in a wheelchair for the rest of life. Dealing with the new outbreak of COVID 19 pneumonia, it is necessary to learn the lessons of SARS treatments and to avoid the overuse of glucocorticoids.

It is imperative to search for effective and non-toxic strong anti-inflammatory agents to against pneumonia/pneumonitis/pulmonary fibrosis induced by various chemicals (anticancer targeted/immune therapy) and pathogens.

In fact, licorice (*Glycyrrhiza* GRbra) has been used for thousands of years and is indispensable in traditional Chinese medicine. Glycyrrhizic acid is also widely used as a flavoring agent in the United States and Europe. Glycyrrhizic acid (GR) has been approved by the State Food and Drug Administration of China for the treatment of chronic hepatitis and cirrhosis.

Glycyrrhetinic acid (GA), a pentacyclic triterpenoid derivative that forms the functional motif of GR, has been studied for the treatment of inflammation, peptic ulcer and other conditions.

GR/GA and related compounds, however, have not previously been reported to play any role in the mitigation or/and treatment of pneumonitis/pneumonia or/and pulmonary fibrosis induced by our newly developed model system.

BRIEF SUMMARY OF THE INVENTION

The present invention pertains to novel uses of glycyrrhetinic acid (GA), glycynthizic acid (GR) and related compounds for mitigation and/or treatment of pneumonitis/pneumonia/pulmonary fibrosis induced by various chemicals (e.g., anticancer targeted/immune therapy) and pathogens.

The method comprises administering (as drug, health products, foods or food additives), to a subject in need of such mitigation/treatment, an effective amount of one or more of the compounds and compositions of the present invention.

Also described are therapeutic uses of prodrugs, metabolites, derivatives (e.g., acids, esters and ethers), and salts of glycyrrhetinic acid (GA).

BRIEF DESCRIPTION OF THE DRAWINGS

FIG. 1 shows the structural similarity of glycyrrhetinic acid (GA)/glycyrrhetinic acid (GR) and glucocorticoids.

FIGS. 3A-3C show that the new method delivers drug evenly to lung lobes of left and right sides and causes pneumonitis and GR/GA treatment effects evidenced by lung index and HE staining in ICR model.

FIGS. 9A-9H show that GA or/and GR reduces the white blood cell (WBC) in various chemicals-induced lung damage, indicating a systemic effect of GR/GA on anti-inflammation.

FIGS. 13A-13D show that GR/GA reduces number of neutrophils in various chemicals-induced pneumonitis, indicating a systemic effect of GR/GA on anti-inflammation. With reduction of neutrophils and increase of lymphocytes, GR/GA could reduce NLR (ratio of neutrophils to lymphocytes), a good sign for host immunity and good prognosis, which is not seen with dexamethasone and Ribavirin.

FIG. 14 shows that GA reduces the tumor growth in tumor bearing mice, indicating that GA/GR have no side-effect on promoting tumor growth and can be safely in cancer treatment concurrent with other drugs.

FIGS. 15A-15B show that GA GA reduces the growth of tumor in the tumor bearing mice treated with active immunotherapy, indicating that GA/GR could be used in combination with active immunotherapy without other adverse effects.

FIG. 16 shows that GA improves the survival rate of tumor bearing mice with active immunotherapy, indicating that GA/GR can be used in combination with immunotherapy without side effects.

FIG. 17 shows that GR mitigates EGFR-targeted drug Osimertinib-induced pneumonitis in a lung cancer patient.

FIGS. 21A-21H show a new process for alteration analysis of CT density before and after treatments of lung damage. To objectively and precisively determine the effects of anti-lung damage drugs, the CT must be taken with a similar anatomic imaging and then with 6 steps for automatic segmentation analysis of alteration of lung density as determined by pixel before and after treatments.

FIGS. 22A-22D and 23 show the differences in pharmacokinetics (PK) between GR and GA. GA absorption is much faster (Tmax GA 0.5 hr vs GR 12 hr) and at a higher level (Cmax GA 49096 vs GR 10842) when same mole of dose given orally. PK difference should be taken into consideration when both GR and GA are developing into drugs.

DETAILED DISCLOSURE OF THE INVENTION

Figure 2A:
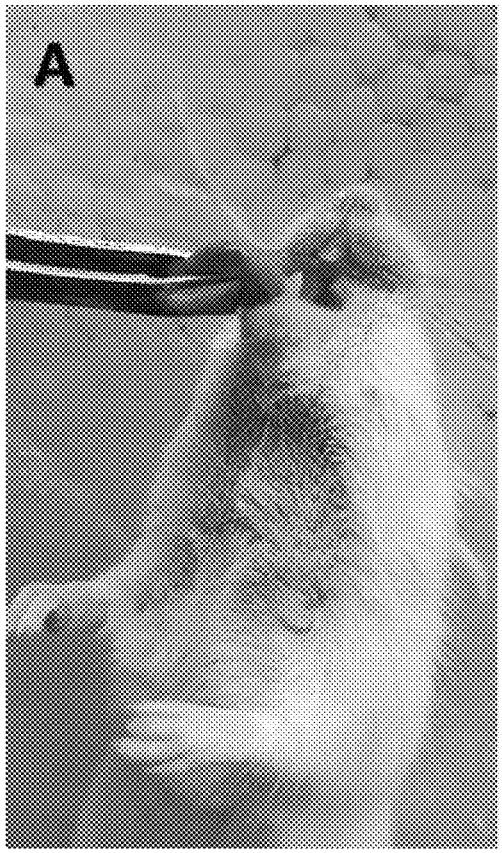
FIGS. 2A-2B show a new method for induction of lung inflammation/damage with various chemicals (anti-cancer agents and paraquat, etc.) in a mouse model.

The present invention pertains to novel uses of glycyrrhizic acid (GR), glycyrrhetinic acid (GA), and related compounds for the mitigation/treatment of pneumonitis/pneumonia/pulmonary fibrosis induced by various chemicals (e.g., anticancer targeted/immune therapy) and pathogens. Also described are therapeutic uses of prodrugs, metabolites, derivatives (e.g., acids, esters and ethers), and salts of glycyrrhetinic acid (GA) and glycyrrhizic acid (GR).

The subject invention pertains to the use of glycyrrhizic acid or glycyrrhetinic and related compounds for mitigation and/or treatment of pneumonia/pneumonitis/pulmonary fibrosis induced by various chemicals (anticancer targeted/immune therapy) and pathogens in a way that is different from dexamethasone and Ribavitin.

The main components of glycyrrhizic acid (GR) and related compounds (such as its salt form with ammonium, potassium, sodium, magnesium salt, etc., oral dose range of 150-600 mg per day for adults) or glycyrrhetinic acid (GA) and related compounds (functional group of GR, oral dose range of 100-400 mg per day for adults). The anti-pneumonia/pneumonitis/pulmonary fibrosis agents above can be used for 7-90 days.

Glycyrrhetinic acid, glycyrrhizic acid and related compounds can also be used to prepare health products, foods or food additives for the prevention, mitigation and/or treatment of pneumonia/pulmonary fibrosis induced by various chemicals (targeted/immune therapy) and pathogens.

This invention also provides: 1) a fast and effective mouse assay procedure to evaluate chemicals used in drug discovery against lung damage; 2) an automatic segmentation analysis for alterations of CT density before and after treatments of lung damage for objective and precise determination of drug efficacy. In addition, the differences in pharmacokinetics (PK) between GR and GA are also defined for the strategy of clinical use of GR and GA.

In one embodiment, the method comprises administering (as drug, health products, foods or food additives), to a subject in need of such treatment, an effective amount of the compounds and compositions of the present invention. The present invention can also be used to mitigate/treat lung diseases induced by various chemicals and pathogens.

Compounds

The present invention pertains to therapeutic uses of glycyrrhetinic acid (GA), glycyrrhizic acid (GR) and related compounds. Also described are therapeutic uses of prodrugs, metabolites, derivatives (e.g., acids, esters and ethers), and salts of glycyrrhetinic acid (GA) and glycyrrhizic acid (GR).

It has now been discovered that GA and GR effectively suppress lung inflammation, alleviate pulmonary injury, reduce lung wet weight by preventing the plasma exudation and inflammatory cell infiltration and significantly reduces levels of pulmonary-specific inflammatory mediators (e.g., IL-6, MPO, etc) during the acute (~1 week) and sub-acute (2-3 weeks) phases of pneumonitis. In addition, GR/GA GA significantly suppresses the expression of TGFβ and the collagen I, which promotes the transition of pneumonitis into pulmonary fibrosis.

In one embodiment, the present invention pertains to glycyrrhetinic acid (GA) (MW: 470.68), having the following structure (Structure A):

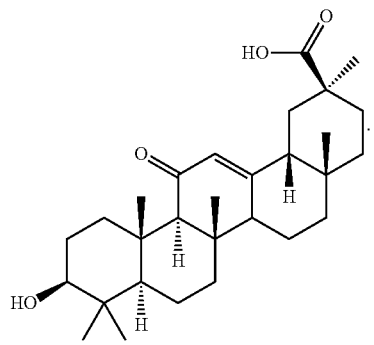

In another embodiment, the present invention pertains to glycyrrhizic acid (GR) (MW: 822.93), a triterpenoid saponin glycoside of glycyrrhetinic acid, having the following structure (Structure B):

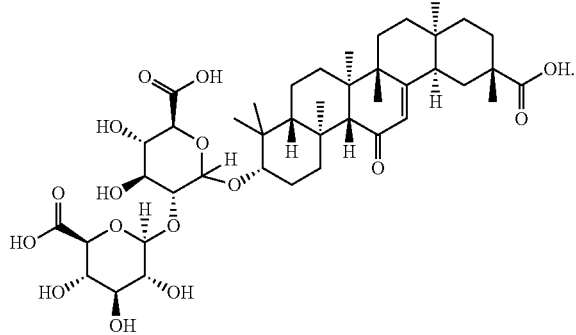

Glycyrrhizic acid can be isolated from the root of liquorice (*Glycyrrhiza* GRbra) or other *Glycyrrhiza* species.

In certain embodiments, the present invention pertains to ester and/or ether forms of glycyrrhetinic acid (GA), represented by the following structure (Structure C):

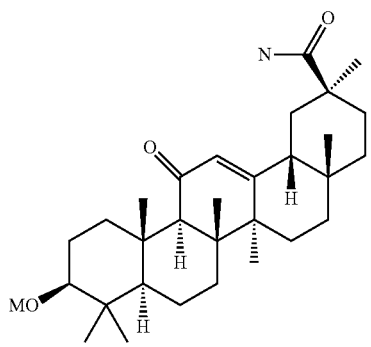

wherein

M represents any group that forms an ether or ester bond with the hydroxy radical; and N represents any group that forms an ester or amide bond with the carboxy group.

In certain embodiments, the present invention pertains to ester forms of glycyrrhizic acid (GR), represented by the following structure (Structure D):

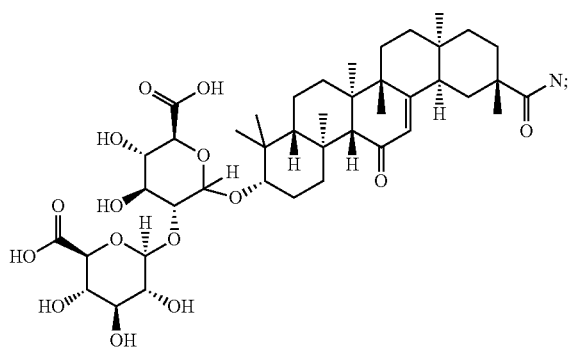

wherein N represents any group that forms an ester or amide bond with the carboxy group.

In certain embodiments, M can be alkyl, substituted alkyl (e.g., haloalkyl and hydroxyalkyl), alkenyl, substituted alkenyl, —COOH, acyl, alkylcarbonyl, benzyl, cyclic alkyl, or cyclic alkenyl.

In certain embodiments, M can be an organic or inorganic acid group including, but not limited to, acetic acid, carboxylic acid, aspartic acid, formic acid, citric acid, benzoic acid, hippuric acid, malic acid, mucic acid, phosphoric acid, sulfuric acid, gluconic acid, maleic acid, succinic acid, tartaric, and lactic acid.

In certain embodiments, M can be a carbohydrate moiety, in which a monosaccharide, disaccharide, oligosaccharide, or its derivative loses an —H in its hydroxyl group and thereby forms a radical. Suitable carbohydrate moieties can be derived, for example, from glucose, fructose, and sucrose.

In certain embodiments, N can be —$NH_2$, alkylamino, or alkoxy.

"Alkyl" means a linear saturated monovalent radical of one to sixteen carbon atoms or a branched saturated monovalent of three to sixteen carbon atoms. It may include hydrocarbon radicals of one to four or one to three carbon atoms, which may be linear. Examples include methyl, ethyl, propyl, 2-propyl, n-butyl, iso-butyl, tert-butyl, pentyl, and the like.

"Alkenyl" means a linear or branched $C_2$-$C_{16}$ hydrocarbon radical that comprises one or more carbon-carbon double bonds. Examples include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Acyl" means a radical —C(O)R where R is hydrogen, alkyl or cycloalkyl, or heterocycloalkyl. Examples include formyl, acetyl, ethylcarbonyl, and the like.

"Carboxyl" means the radical —C(O)OH.

"Carboalkoxy" means a radical —C(O)R where R is, for example, hydrogen, alkyl or cycloalkyl, heterocycloalkyl, halo, or alkyl halo.

"Halo" means fluoro, chloro, bromo fluoro, chloro, bromo, or iodo, such as bromo and chloro.

"Haloalkyl" means alkyl substituted with one or more same or different halo atoms, e.g., —$CH_2Cl$, —$CH_2Br$, —$CF_3$, —$CH_2CH_2Cl$, —$CH_2CCl_3$, and the like.

"Amino" means the radical —$NH_2$.

"Alkylamino" means a radical —NHR or —$NR_2$ where each R is independently an alkyl group. Examples include methylamino, (1-methylethyl)amino, dimethylamino, methylethylamino, di(1-methyethyl)amino, and the like.

"Hydroxy" means the radical —OH.

"Hydroxyalkyl" means an alkyl radical as defined herein, substituted with one or more, preferably one, two or three hydroxy groups. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxy-propyl, preferably 2-hydroxyethyl, 2,3-dihydroxypropyl and 1-(hydroxymethyl) 2-hydroxyethyl.

"Alkoxy" means the radical —$OR_a$, where $R_a$ is an alkyl group or substituted alkyl group. Exemplary alkoxy groups include methoxy, ethoxy, propoxy, and the like.

In one embodiment, the present invention pertains to acetoxolone ($C_{32}H_{48}O_5$, CAS No. 6277-14-1), an acetyl derivative of glycyrrhizic acid.

The present invention also pertains to salt forms of GA, GR and related compounds including, but not limited to, ammonium salts, sodium salts, and potassium salts.

The present invention also pertains to uses of prodrugs and metabolites of the compounds. The term "prodrug," as used herein, refers to a metabolic precursor of a compound of the present invention or pharmaceutically acceptable form thereof. In general, a prodrug comprises a functional derivative of a compound, which may be inactive when administered to a subject, but is readily convertible in vivo into an active metabolite compound.

Conventional procedures for the selection and preparation of suitable prodrug derivatives are described, for example, in "Design of Prodrugs", ed. H. Bundgaard, Elsevier, 1985. Preferably, a prodrug of the present invention enhances desirable qualities of the compound of the present invention including, but not limited to, solubility, bioavailability, and stability. Hence, the compounds employed in the present methods may, if desired, be delivered in a prodrug form. Prodrugs of the compounds employed in the present invention may be prepared by modifying functional groups present in the compound such that the modifications are cleaved, either in routine manipulation or in vivo, to the parent compound.

The term "metabolite," refers to a pharmacologically active product, including for example, an active intermediate or an ultimate product, produced through in vivo metabolism of a compound of the present invention in a subject. A metabolite may result, for example, from the anabolic and/or catabolic processes of the administered compound in a subject, including but not limited to, the oxidation, reduction, hydrolysis, amidation, deamidation, esterification, deesterification, enzymatic cleavage, and the like.

Metabolites are typically identified by preparing a radio-labelled (e.g., $^{14}C$ or $^{3}H$) isotope of a compound of the present invention, administering it parenterally in a detectable dose (e.g., greater than about 0.5 mg/kg) to an animal such as rat, mouse, guinea pig, monkey, or to a human, allowing sufficient time for metabolism to occur (typically about 30 seconds to about 30 hours), and isolating its conversion products from the urine, blood or other biological samples. These products are easily isolated since they are labeled (others are isolated by the use of antibodies capable of binding epitopes surviving in the metabolite). The structure of metabolites can be determined in conventional fashion, e.g., by MS, LC/MS or NMR analysis. In general, analysis of metabolites is performed according to techniques well known to those skilled in the art of drug metabolism studies.

The present invention further pertains to isolated enantiomeric compounds. The isolated enantiomeric forms of the compounds of the invention are substantially free from one another (i.e., in enantiomeric excess). In other words, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. In one embodiment of the invention, the isolated enantiomeric compounds are at least about in 80% enantiomeric excess. In a preferred embodiment, the compounds are in at least about 90% enantiomeric excess. In a more preferred embodiment, the compounds are in at least about 95% enantiomeric excess. In an even more preferred embodiment, the compounds are in at least about 97.5% enantiomeric excess. In a most preferred embodiment, the compounds are in at least about 99% enantiomeric excess.

In an embodiment, the compounds of the present invention have the same chiral structure as shown in any of Structures A-D.

Prevention and/or Treatment of Pulmonary Fibrosis

The present invention provides methods for prevention and/or treatment of pulmonary fibrosis, in particular, irradiation-induced pulmonary fibrosis. The present methods can also be used to prevent, treat or ameliorate lung diseases associated with pulmonary fibrosis.

In one embodiment, the method comprises administering, to a subject in need of such treatment, an effective amount of the compounds and compositions of the present invention. Preferably, the compounds and compositions of the present invention are prepared in a form for administration to the lungs.

The term "pulmonary fibrosis" or "lung fibrosis", as used herein, refers to abnormal formation or accumulation of fibrous, connective, or scar tissues and/or matrix macromolecules (e.g., collagens, fibronectins, proteoglycans) on and/or within lungs. Symptoms of pulmonary fibrosis include shortness of breath, dry cough, increased respiratory rate, decreased lung compliance, increased lung density, chest discomfort, and rapid weight loss. Pulmonary fibrosis does not encompass any fibrotic condition that develops in organs other than lungs, such as fibrotic conditions that develop in the liver.

The term "treatment" or any grammatical variation thereof (e.g., treat, treating, and treatment etc.), as used herein, includes but is not limited to, ameliorating or alleviating a symptom of a disease or condition, reducing, suppressing, inhibiting, lessening, or affecting the progression, severity, and/or scope of a condition. In one embodiment, treatment refers to reducing, suppressing, inhibiting, lessening, or affecting the progression, severity, and/or scope of abnormal formation or accumulation of fibrous, connective, or scar tissues and/or matrix macromolecules (e.g., collagens, fibronectins and proteoglycans) on or within lungs.

The term "prevention" or any grammatical variation thereof (e.g., prevent, preventing, and prevention etc.), as used herein, includes but is not limited to, delaying the onset of symptoms, preventing relapse to a disease, increasing latency between symptomatic episodes, or a combination thereof. Prevention, as used herein, does not require the complete absence of symptoms.

Lung diseases associated with pulmonary fibrosis include complications of pulmonary fibrosis, lung diseases that would develop into pulmonary fibrosis, and lung diseases that arise from pulmonary fibrosis. Symptoms and complications of pulmonary diseases include, but are not limited to, hypoxemia, dyspnea, othopnea, cyanosis, pulmonary hypertension, corpulmonale, and lung dysfunction. Lung conditions that could develop into pulmonary diseases include, but are not limited to, injury to lungs (e.g., irradiation, chemicals, medications, biological injury and pollutants), lung infection (e.g., viral, bacterial and fungal infection), interstitial lung diseases, parasite-damage and pneumonitis.

"Pneumonitis," as used herein, refers to its ordinary meaning, that, is inflammation of lung tissue.

The term "effective amount," as used herein, refers to an amount that is capable of preventing, ameliorating, or treating pulmonary fibrosis. For instance, an effective amount is an amount capable of alleviating one or more symptoms of pulmonary fibrosis. In certain embodiments, the effective amount enables at least 5%, 10%, 15%, 20%, 25%, 30%, 35%, 40%, 45%, 50%, 60%, 70%, 80%, 90%, or 100% decrease in respiratory rate, decrease in lung density, increase in body weight, and/or increase in lung compliance, as compared to non-treated subjects with pulmonary fibrosis.

In a specific embodiment, the effective amount enables at least 5%, 10%, 15%, 20%, 25%, 30%, 35%, 40%, 45%, 50%, 60%, 70%, 80%, 90%, or 100% reduction in abnormal accumulation of fibrous materials (e.g., collagens, fibronectins and proteoglycans) in lungs, as compared to non-treated subjects with pulmonary fibrosis. For instance, the effective amount enables at least 5%, 10%, 15%, 20%, 25%, 30%, 35%, 40%, 45%, 50%, 60%, 70%, 80%, 90%, or 100% reduction in collagen, fibronectin, proteoglycan or hydroxyproline content in lungs, as compared to non-treated subjects with pulmonary fibrosis. For another instance, the effective amount enables at least 5%, 10%, 15%, 20%, 25%, 30%, 35%, 40%, 45%, 50%, 60%, 70%, 80%, 90%, or 100% reduction in pro-fibrotic mediators such as TGF$\beta$ in lung tissue, as compared to non-treated subjects with pulmonary fibrosis.

Additionally, as pulmonary fibrosis arises, in many instances, from inflammatory responses to lung injury or infection, an effective amount is capable of reducing the levels of one or more pulmonary inflammatory mediators, including SP-D, IL1$\alpha$, TNF$\alpha$, IL6, PF4, P-selectin, L-selectin, VCAM-1, lymphotactin, and prostaGRndin E (PGE). In certain embodiments, the effective amount enables at least 5%, 10%, 15%, 20%, 25%, 30%, 35%, 40%, 45%, 50%, 60%, 70%, 80%, 90%, or 100% reduction in the levels of one or more inflammatory mediators, as compared to non-treated subjects with pulmonary fibrosis.

The term "subject," as used herein, describes an organism, including mammals such as primates, to which treatment with the compositions according to the present invention can be provided. Mammalian species that can benefit from the disclosed methods of treatment include, but are not limited to, apes, chimpanzees, orangutans, humans, monkeys; and domesticated animals such as dogs, cats, horses, cattle, pigs, sheep, goats, chickens, mice, rats, guinea pigs, and hamsters.

"A subject in need of such treatment", as used herein, refers to a subject who is specifically at risk of, has symptoms of, or is diagnosed with, pneumonitis, pneumonia, and/or lung diseases associated with pulmonary fibrosis. In a specific embodiment, the present invention comprises diagnosing whether a subject has pneumonitis, pneumonia, and/or lung diseases, wherein the compounds and compositions of the present invention are administered to the subject who is diagnosed with, or has symptoms of, pneumonitis, pneumonia, and/or lung diseases associated with pulmonary fibrosis.

The identification of subjects who have pneumonitis, pneumonia, and/or lung diseases associated with pulmonary fibrosis is well within the knowledge and ability of one skilled in the art. By way of example, a clinician skilled in the art can readily, by the use of physical exams such as pulmonary function test and exercise test, identify observable symptoms of pneumonitis, pneumonia, and/or lung diseases associated with pulmonary fibrosis. In addition, a combination of medical techniques, such as chest X-day, high resolution computerized tomography (HRCT), and surgical lung biopsy, can be employed to determine the pathological alteration of lung tissues caused by pneumonitis, pneumonia, and/or lung diseases associated with pulmonary fibrosis.

In another embodiment, the compounds and compositions of the present invention are administered to a subject who has no observable symptoms of pneumonitis, pneumonia, and/or lung diseases associated with pulmonary fibrosis, but has been determined to be susceptible to developing pneumonitis, pneumonia, and/or lung diseases associated with pulmonary fibrosis (hereinafter such a patient is referred to as an "at-risk patient"). For instance, "at-risk patients" include subjects who had injury to the lung (e.g., chemicals, medications, biological injury, irradiation and pollutants), lung infection (e.g., viral, bacterial and fungal infection), and diseases such as pneumonitis and interstitial lung diseases. In a specific embodiment, a patient is assessed to identify the risk of developing pneumonitis, pneumonia, and/or lung diseases associated with pulmonary fibrosis, prior to the administration of the compounds and compositions of the present invention. In a further specific embodiment, the subject is a cancer patient who received, or is receiving, medications for cancer treatment.

In an embodiment, the compounds and pharmaceutical compositions of the present invention can be used to prevent, treat or ameliorate pneumonitis, pneumonia, and/or lung diseases associated with pulmonary fibrosis.

In one embodiment, the compounds and pharmaceutical compositions of the present invention can be used to prevent, treat or ameliorate pneumonitis, pneumonia, and/or lung diseases associated with pulmonary fibrosis induced by chemicals (including anticancer drugs, targeted small molecules, immunotherapy, drugs for various diseases), pollutants, toxins, trauma, cigarette smoking, autoimmune diseases such as rheumatoid arthritis, medications (e.g., amiodarone, bleomycin, busulfan, methotrexate, and nitrofurantoin), asbestos, and infection (e.g. viral, bacterial and fungal infection).

In one embodiment, the compounds and pharmaceutical compositions of the present invention can be used to prevent, treat or ameliorate disease that would develop into pneumonitis and/or lung diseases associated with pulmonary fibrosis, including interstitial lung diseases, acute and/or chronic pneumonitis, chronic obstructive pulmonary disease (COPD), asthma, silicosis, lung injury, and pneumonia.

In one embodiment, the compounds and pharmaceutical compositions of the present invention can be used to prevent, treat or ameliorate inflammation and fibrotic diseases or conditions that develop in skin, heart, intestine, and/or retroperitoneum. In an embodiment, the present invention excludes treatment of hepatitis/liver fibrosis induced by virus, alcohol. Medications, chemicals and radiation.

While in the experimental models of the present invention pneumonitis, pneumonia and/or lung diseases associated with pulmonary fibrosis were induced using chemicals/virus, it would be readily understood that the therapeutic benefits of the present invention extend beyond chemicals/virus.

Therapeutic Compositions and Formulations

The present invention also provides for therapeutic or pharmaceutical compositions comprising a compound of the invention in a form that can be combined with a pharmaceutically acceptable carrier. In this context, the compound may be, for example, isolated or substantially pure. The present invention also embodies nutritional supplements and health food or drink formulations comprising a compound of the invention.

The term "carrier" refers to a diluent, adjuvant, excipient, or vehicle with which the compound is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers, particularly for injectable solutions. Particularly preferred pharmaceutical carriers for treatment of or amelioration of inflammation in the central nervous system are carriers that can penetrate the blood/brain barrier.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The therapeutic composition, if desired, can also contain minor amounts of wetting or emulsifying agents, or pH buffering agents. These compositions can take the form of solutions, suspensions, emulsion, tablets, capsules, powders, sustained-release formulations and the like. The composition can be formulated with traditional binders and carriers such as triglycerides. Examples of suitable pharmaceutical carriers are described in "Remington's Pharmaceutical Sciences" by E. W. Martin. Such compositions contain a therapeutically effective amount of the therapeutic composition, together with a suitable amount of carrier so as to provide the form for proper administration to the patient. The formulation should suit the mode of administration.

In preferred embodiments, the compositions are prepared in a form adapted for delivery into the lungs. For instance, the liquid pharmaceutical composition may be lyophilized prior to use in pulmonary delivery, where the lyophilized composition is milled to obtain the finely divided dry powder consisting of particles within a desired size range noted above. For another instance, spray-drying may be used to obtain a dry powder form of the liquid pharmaceutical composition, and the process is carried out under conditions that result in a substantially amorphous finely divided dry powder consisting of particles within the desired size range. For methods of preparing dry powder forms of pharmaceutical compositions, see, for example, WO 96/32149; WO 97/41833; WO 98/29096; and U.S. Pat. Nos. 5,976,574; 5,985,248; 6,001,336; and 6,875,749 herein incorporated by reference. In addition, the dry powder form of the pharmaceutical composition may be prepared and dispensed as an aqueous or nonaqueous solution or suspension, in a metered-dose inhaler.

In addition, a pharmaceutically effective amount of the dry powder form of the composition may be formulated as an aerosol or other preparation suitable for pulmonary inhalation. The amount of dry powder form of the composition placed within the delivery device is sufficient to allow for delivery of a pharmaceutically effective amount of the composition to the subject by inhalation. The delivery device delivers, in a single or multiple fractional doses, by pulmonary inhalation a pharmaceutically effective amount of the composition to the subject's lungs. The aerosol propellant may be any conventional material employed for this purpose.

When used in the context of pharmaceutical compositions suitable for pulmonary delivery, these terms have the following intended meaning. By "aqueous" is intended a composition prepared with, containing, or dissolved in water, including mixtures wherein water is the predominating substance in the mixture. By "nonaqueous" is intended a composition prepared with, containing, or dissolved in a substance other than water or mixtures wherein water is not the predominating substance in the mixture. By "solution" is intended a homogeneous preparation of two or more substances, which may be solids, liquids, gases, or intercombinations thereof. By "suspension" is intended a mixture of substances such that one or more insoluble substances are homogeneously dispersed in another predominating substance.

For purposes of the present invention, the terms "solid" and "dry powder" are used interchangeably with reference to the pharmaceutical compositions. By "solid" or "dry powder" form of a pharmaceutical composition is intended the composition has been dried to a finely divided powder having a moisture content below about 10% by weight, usually below about 5% by weight, and preferably below about 3% by weight. This dry powder form of the composition consists of particles comprising the peptides of the subject invention. Preferred particle sizes are less than about 90.0 µm mean diameter, more preferably less than about 70.0 µm, more preferably less than about 50.0 µm even more preferably about less than about 30.0 µm, more preferably less than about 10.0 µm, more preferably less than about 7.0 µm, even more preferably in the range of 0.1 to 5.0 µm, most preferably in the range of about 1.0 to about 5.0 µm diameter.

A surfactant may be added to the pharmaceutical composition to reduce adhesion of the dry powder to the walls of the delivery device from which the aerosol is dispensed. Suitable surfactants for this intended use include, but are not limited to, sorbitan trioleate, soya lecithin, and oleic acid. Devices suitable for pulmonary delivery of a dry powder form of a composition as a nonaqueous suspension are commercially available. Examples of such devices include the Ventolin metered-dose inhaler (GRxo Inc., Research Triangle Park, N.C.) and the Intal Inhaler (Fisons, Corp., Bedford, Mass.). See also the aerosol delivery devices described in U.S. Pat. Nos. 5,522,378; 5,775,320; 5,934,272; and 5,960,792 herein incorporated by reference.

In yet another embodiment, the pharmaceutical composition can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; and Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the composition's target, i.e., the lung, thus requiring only a fraction of the systemic dose (see, e.g., Goodson, in Medical Applications of Controlled Release, supra, vol. 2, pp. 115-138 (1984).

In one embodiment, the composition is formulated in accordance with routine procedures as a pharmaceutical composition adapted for local injection administration to human beings. Typically, compositions for local injection administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is administered by injection, an ampoule of sterile water for injection or saline can be provided so that the ingredients may be mixed prior to administration.

The therapeutic or pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The present invention also provides for the modification of the compound such that it is more stable once administered to a subject, i.e., once administered it has a longer time period of effectiveness as compared to the unmodified compound. Such modifications are well known to those of skill in the art, e.g., microencapsulation, etc.

The invention also provides a pharmaceutical pack or kit comprising one or more containers filled with one or more of the ingredients, e.g., compound, carrier, of the pharmaceutical compositions of the invention.

The compounds of the present invention can also be formulated consistent with traditional Chinese medicine practices. The composition and dosage of the formulation that are effective in the treatment of a particular disease, condition or disorder will depend on the nature of the disease, condition or disorder by standard clinical techniques.

The traditional Chinese medicine in prescription amounts can be readily made into any fol. ii of drug, suitable for administering to humans or animals. Suitable forms include, for example, tinctures, decoctions, and dry extracts. These can be taken orally, applied through venous injection or mucous membranes. The active ingredient can also be formulated into capsules, powder, pallets, pastille, suppositories, oral solutions, pasteurized gastroenteric suspension injections, small or large amounts of injection, frozen powder injections, pasteurized powder injections and the like. All of the above-mentioned methods are known to people skilled in the art, described in books and commonly used by practitioners of herbal medicine.

A tincture is prepared by suspending herbs in a solution of alcohol, such as, for example, wine or liquor. After a period of suspension, the liquid (the alcohol solution) may be administered, for example, two or three times a day, one teaspoon each time.

A decoction is a common form of herbal preparation. It is traditionally prepared in a clay pot, but can also be prepared in GRss, enamel or stainless steel containers. The formulation can be soaked for a period of time in water and then brought to a boil and simmered until the amount of water is reduced by, for example, half.

An extract is a concentrated preparation of the essential constituents of a medicinal herb. Typically, the essential constituents are extracted from the herbs by suspending the herbs in an appropriate choice of solvent, typically, water, ethanol/water mixture, methanol, butanol, iso-butanol, acetone, hexane, petroleum ether or other organic solvents. The extracting process may be further facilitated by means of maceration, percolation, repercolation, counter-current extraction, turbo-extraction, or by carbon-dioxide hyper-critical (temperature/pressure) extraction. After filtration to rid of herb debris, the extracting solution may be further evaporated and thus concentrated to yield a soft extract (extractum spissum) and/or eventually a dried extract, extracum siccum, by means of spray drying, vacuum oven drying, fluid-bed drying or freeze-drying. The soft extract or dried extract may be further dissolved in a suitable liquid to a desired concentration for administering or processed into a form such as pills, capsules, injections, etc.

Routes of Administration

The compounds and compositions of the subject invention can be administered to the subject being treated by standard routes, including oral, inhalation, or parenteral administration including intravenous, subcutaneous, topical, transdeiinal, intradermal, transmucosal, intraperitoneal, intramuscular, intracapsular, intraorbital, intracardiac, transtracheal, subcutaneous, subcuticular, intraarticular, subcapsular, subarachnoid, intraspinal, epidural and intrasternal injection, infusion, and electroporation, as well as co-administration as a component of any medical device or object to be inserted (temporarily or permanently) into a subject.

In preferred embodiments, the compounds and compositions of the subject invention are administered in any route suitable for pulmonary delivery. Pulmonary administration requires dispensing of the biologically active substance from a delivery device into a subject's oral cavity during inhalation. For purposes of the present invention, pharmaceutical compositions can be administered via inhalation of an aerosol or other suitable preparation that is obtained from an aqueous or nonaqueous solution or suspension form, or a solid or dry powder form of the pharmaceutical composition, depending upon the delivery device used. Pulmonary inhalation results in deposition of the inhaled composition in the alveoli of the subject's lungs. Once deposited, the compounds or compositions may be absorbed, passively or actively, across the alveoli epithelium and capillary epithelium layers into the bloodstream.

The amount of the therapeutic or pharmaceutical composition of the invention which is effective in the treatment of a particular disease, condition or disorder will depend on the route of administration, and the seriousness of the disease, condition or disorder, and should be decided according to the judgment of the practitioner and each patient's circumstances. In general, the dosage ranges from about 0.001 mg/kg to about 3 g/kg. For instance, suitable unit dosages may be between about 0.01 to about 3 g, about 0.01 to about 1 g, about 0.01 to about 500 mg, about 0.01 to about 400 mg, about 0.01 to about 300 mg, about 0.01 to about 200 mg, about 0.01 to about 100 mg, about 0.01 to about 50 mg, about 0.01 to about 30 mg, about 0.01 to about 20 mg, about 0.01 to about 10 mg, about 0.01 to about 5 mg, about 0.01 to about 3 mg about, 0.01 to about 1 mg, or about 0.01 to about 0.5 mg. Such a unit dose may be administered more than once a day, e.g. two or three times a day.

The amount of active ingredient that may be combined with the carrier materials to produce a single dosage form will vary, depending such as the type of the condition and the subject to be treated. In general, a therapeutic composition contains from about 5% to about 95% active ingredient (w/w). More specifically, a therapeutic composition contains from about 20% (w/w) to about 80% or about 30% to about 70% active ingredient (w/w).

Once improvement of the patient's condition has occurred, a maintenance dose is administered if necessary. Subsequently, the dosage or the frequency of administration, or both, may be reduced as a function of the symptoms to a level at which the improved condition is retained. When the symptoms have been alleviated to the desired level, treatment should cease. Patients may however require intermittent treatment on a long-term basis upon any recurrence of disease symptoms.

In addition, in vitro assays may optionally be employed to help identify optimal dosage ranges. The precise dose to be employed in the formulation will also depend on the route of administration, and the seriousness of the disease, condition or disorder, and should be decided according to the judgment of the practitioner and each patient's circumstances. Effective doses may be extrapolated from dose-response curves derived from in vitro or animal model test systems.

Following are examples that illustrate procedures for practicing the invention. These examples should not be construed as limiting.

Example 1—Structural Similarity of Glycyrrhetinic Acid (GA)/Glycyrrhetinic Acid (GR) and Glucocorticoids After oral administration of glycyrrhizic acid (glucoside, water soluble, GR), it is converted into glycyrrhetinic acid (aglycone, fat soluble, absorbed through double lipid layer, GA) by glucosidase. Glycyrrhetinic acid is the functional group of glycyrrhizic acid.

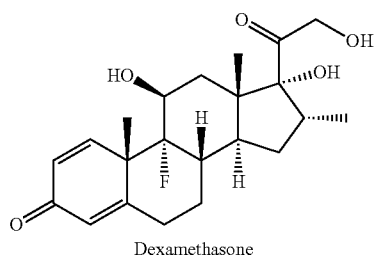

Dexamethasone

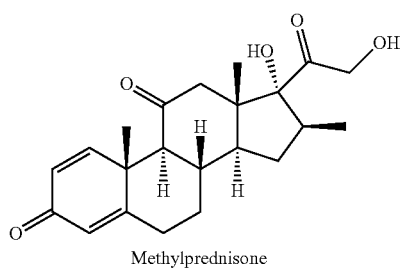

Methylprednisone

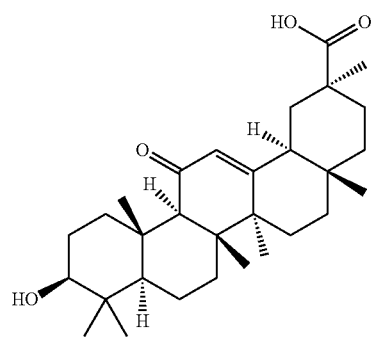

Glycyrrhetinic acid (GA, aglycone, liposoluble, intracellular)

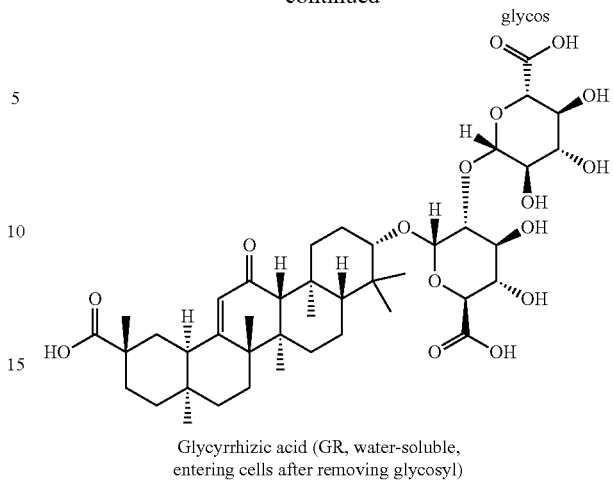

Glycyrrhizic acid (GR, water-soluble, entering cells after removing glycosyl)

Example 2—A New Method for Various Chemical-Induced Lung Inflammation/Damage in Mouse Model The subject invention provides an easy-perform mouse model with inhalation of 110-130 ul of liquid dissolved with various chemicals (e.g., anti-cancer drug or toxic paraquat) deep into whole lung to induce chemicals-pneumonitis. Compared with currently used intratracheal instillation, this new method is more quick (finished within 3 minutes) and non-invasion without surgically exposing the trachea. It delivers agents using a micropipette into the trachea at the back of the throat and allows the mouse to inhale into the lung with operator help for liquid deep-even distribution in the whole lung. This easy operation can quickly set-up for more than one hundred mice with chemicals-pneumonitis, providing enough mice for the screening or validating of various chemical or biological agents for anti-lung inflammation/infection to meet clinical needs.

The procedures are as following:

A. After anesthesia, a rubber band was attached to the front teeth of the mice, and the mouse body was vertically upright. The tip of the tongue was pulled out with forceps, and 100-130 ul of liquid reagent was dripped into the upper part of the trachea at the back of the throat. The reagent was naturally inhaled into the mouse lung. Deep breathing was seen for 3-5 times to ensure that the liquid was deeply inhaled into lung, and then the mice were immediately removed and to be held in hand of operator. Entire process was about one minute.

B. The mouse held firmly in the hands of the operator, moved up and down for 3-5 times to let the liquid moving deep into the lung, rotated around for 2-3 circles and repeated for 3 times to let the liquid evenly distributed in the lung. Entire process was about one minute.

Example 3—New Method Delivers Drug Evenly to Lung Lobes of Left and Right Sides

Figure 3A:
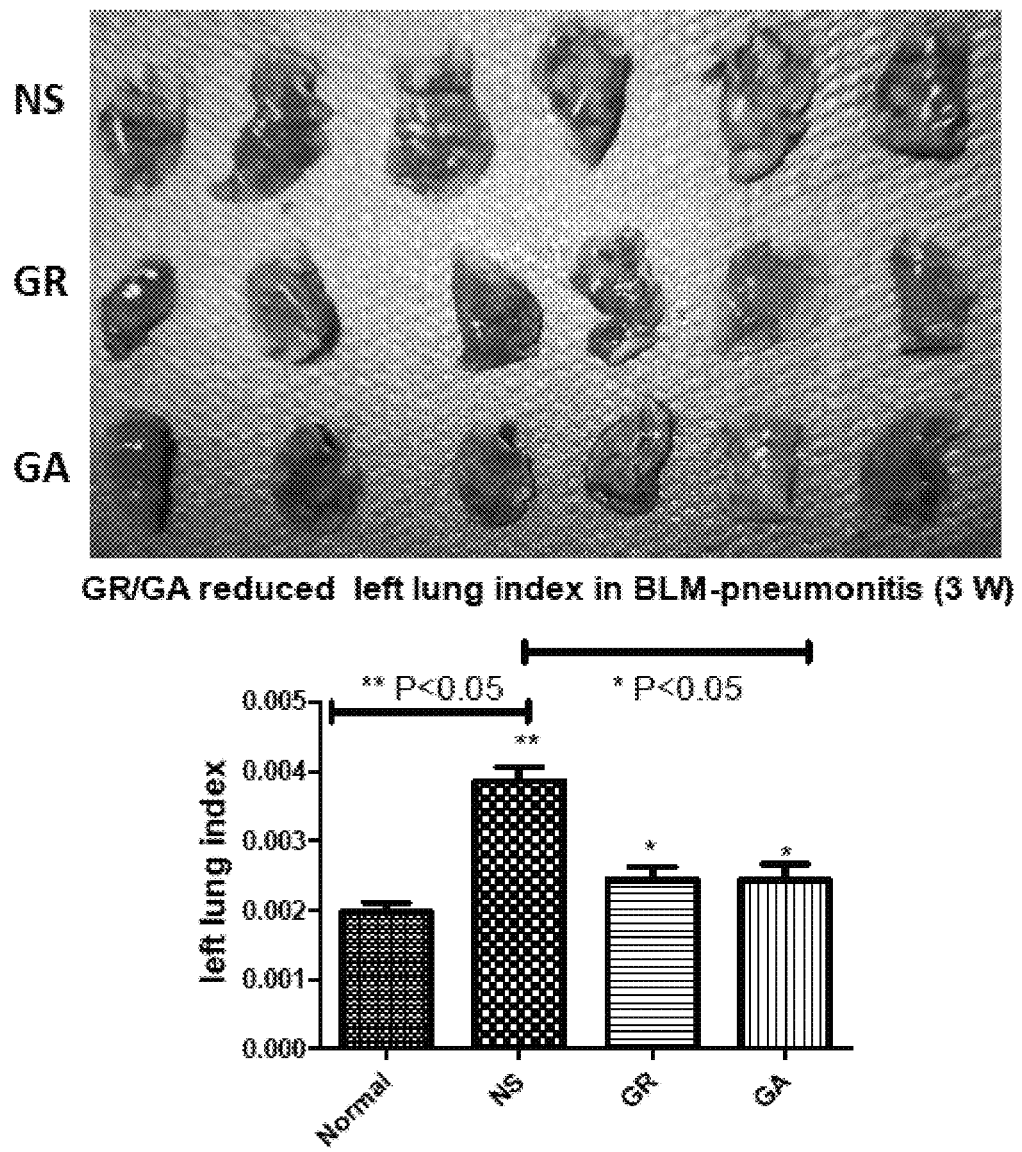

To prove that the new method could deliver drug evenly to whole lung, ICR mice were anesthetized and inhaled 110 ul of 5 mg/ml Bleomycin (BLM) to induce pneumonitis. Then, the mice were randomly divided into three groups (6 mice/group) and orally given different agents: 1) NS: vehicle of saline; 2) GR: 122 mg/kg/day of GR; 3) GA: 67 mg/kg/ day of GA. Three weeks later, mice were sacrificed and the lung lobes of left and right sides were harvested separately. As shown in FIGS. 3A and B, the lung lobes of both left and right sides in mice receiving BLM but treated with saline as vehicle control were big, bloated and heavy in all 6 mice compared to normal mice, indicating that there was severe lung inflammation due to BLM evenly delivered into whole lung causing pneumonitis, which was greatly reduced by GR and GA as evidenced by the significantly reduced lung sizes and lung index (lung wet weight/body weight) in both left side (FIG. 3A) and right side (FIG. 3B). The standard deviations in each group were relatively small, indicating that the new method created model system for chemicals-delivering into lung is consistent and repeatable.

Figure 3C:
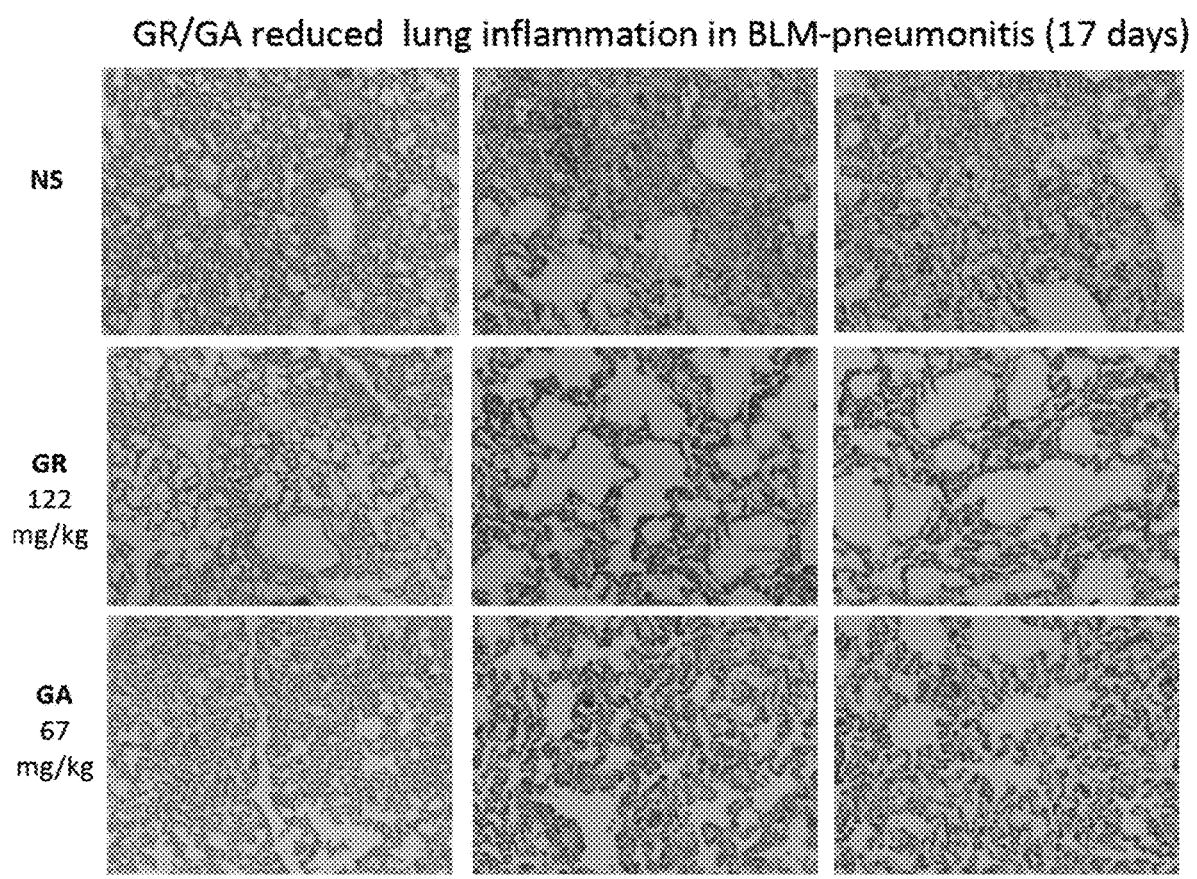

The BLM-pneumonitis (NS) and GR/GA treatment effect (less infiltration of inflammation cells and better lung structure) were also demonstrated by pathology HE staining (FIG. 3C).

Figure 2B:
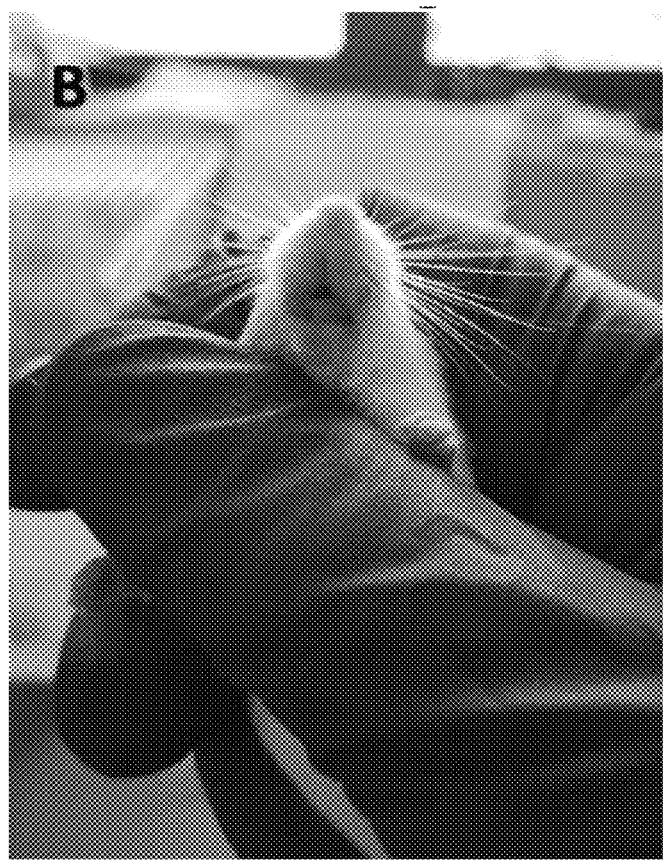

Example 4—Different Doses of GR/GA Reduce Lung Index Increased by BLM-Pneumonitis in C57BL/6 Mice C57BL/6 mice (8 weeks, male) were anesthetized and inhaled 110 ul of 5 mg/ml Bleomycin (BLM) to induce BLM-pneumonitis (new method in FIG. 2). Then, the mice were randomly divided into groups (7 mice/group) and orally given different agents: 1) Normal: as time control without any treatment; 2) NS: treated with saline as vehicle control (all agents in saline); 3) Dexamethasone: 1 mg/kg/day of Dexamethasone; 4) GR: at the indicated three different doses of GR; 5) GA: at the indicated three different doses of GA. Due to the severe BLM-pneumonitis, the inflammatory factors (such as MPO, IL 6 etc.) were released to cause acute reactions: dilation of alveolar capillaries, increased permeability, plasma exudation, blood cells entering the lung interstitium/alveoli, resulting in an increased wet weight of whole lung. The lung index was calculated as: whole lung wet weight/body weight. The higher of lung index, the severer of pneumonitis.

The inhalation of BLM solution resulted an increased lung index, which was reduced by Dexamethasone. All doses of GR and GA had the similar reduction effect to Dexamethasone when comparison experiment was performed side-by-side, suggesting that GR or GA as low as 40 or 22 mg/kg/day could reduce the severity of BLM-pneumonitis.

Example 5—Unlike Dexamethasone, GR/GA Increased Body Weight Reduced by BLM-Pneumonitis in C57BL/6 Mice C57BL/6 mice (8 weeks, male) were anesthetized and inhaled 110 ul of 5 mg/ml Bleomycin (BLM) to induce BLM-pneumonitis (new method in FIG. 2). Then, the mice were randomly divided into four groups and orally given different agents: 1) NS: vehicle of saline; 2) Dexamethasone: 1 mg/kg/day of Dexamethasone; 3) GR: 70 mg/kg/day of GR; 4) GA: 22 mg/kg/day of GA. Due to the severe lung inflammation, the body weights of mice were lost during 2 weeks. Compared with normal mice, the body weights of mice in NS group were significantly reduced.

Figure 4:
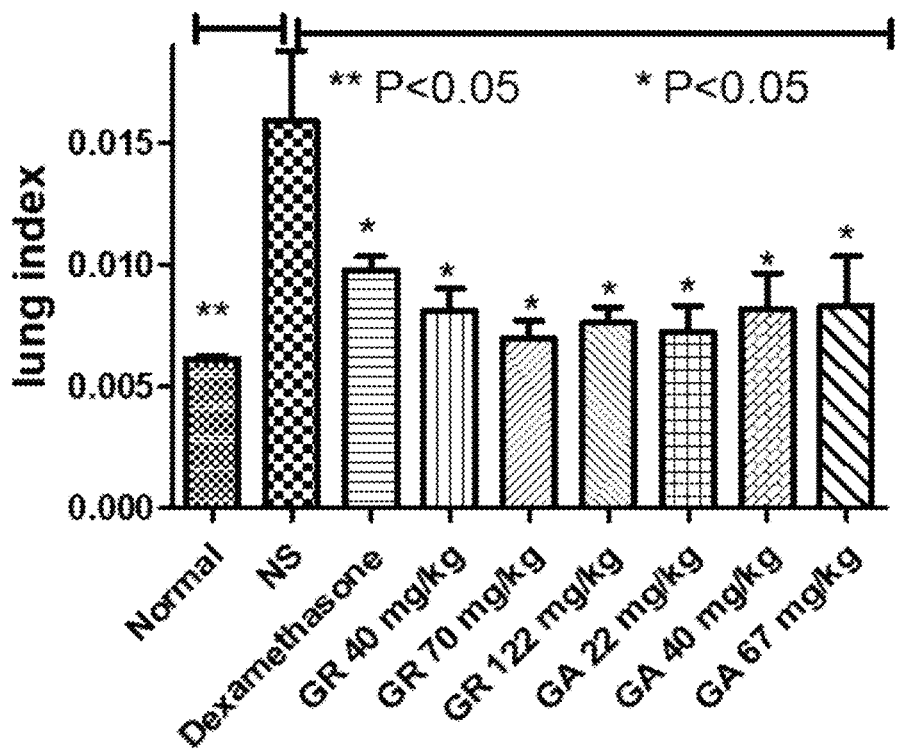
FIG. 4 shows that various doses GR/GA reduces lung index increased by bleomycin-pneumonitis in C57BL/6 mice, and the efficacy is similar to or better than dexamethasone.
Figure 5:
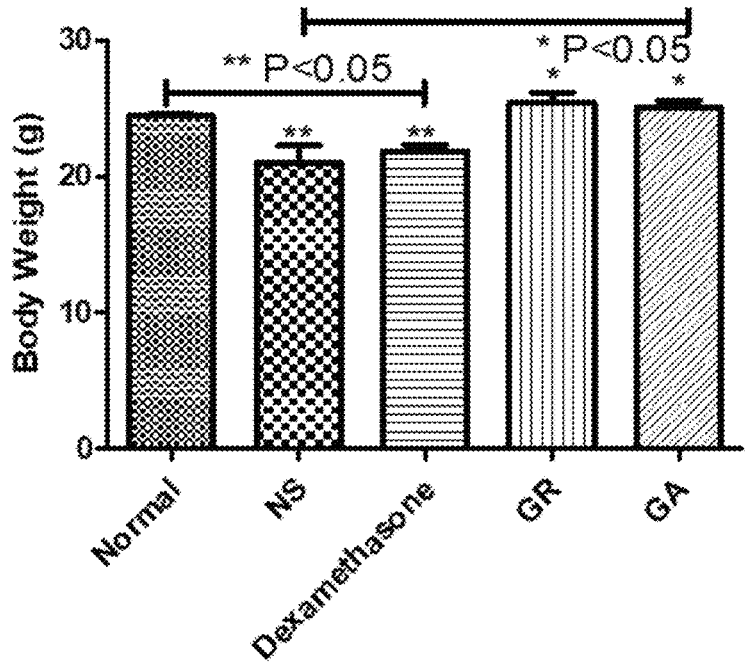
FIG. 5 shows that GR/GA increases body weight reduced by bleomycin-pneumonitis in C57BL/6 mice, while dexamethasone like NS reduced the body weight compared to normal mice.
Figures 6A, 6B:
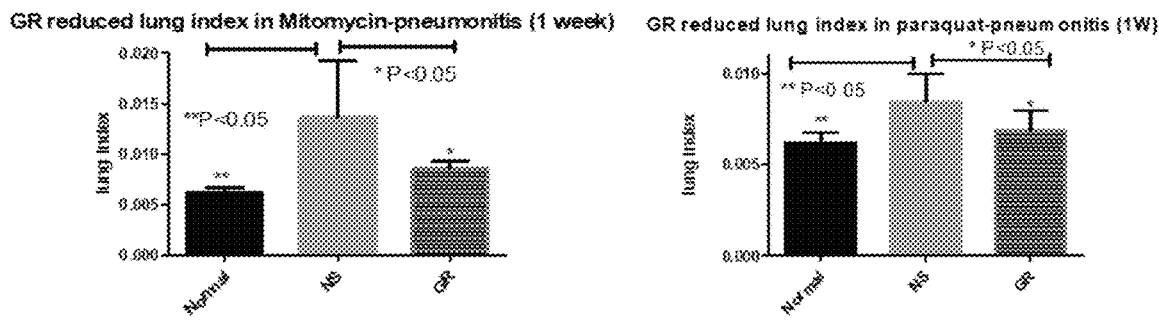
FIGS. 6A-6H show the reduction of the lung index by GR/GA in various chemicals (Mitomycin, Cisplatin, Methotrexate, Bleomycin, Paraquat)-induced pneumonitis in ICR mice, indicating that effect of anti-pneumonitis is reproducible and in a broad spectrum.
Figures 6C, 6D:
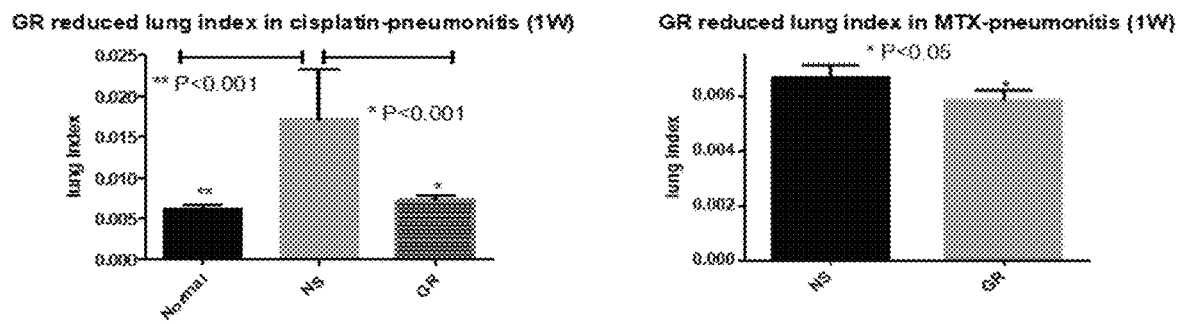
Figures 6E, 6F:
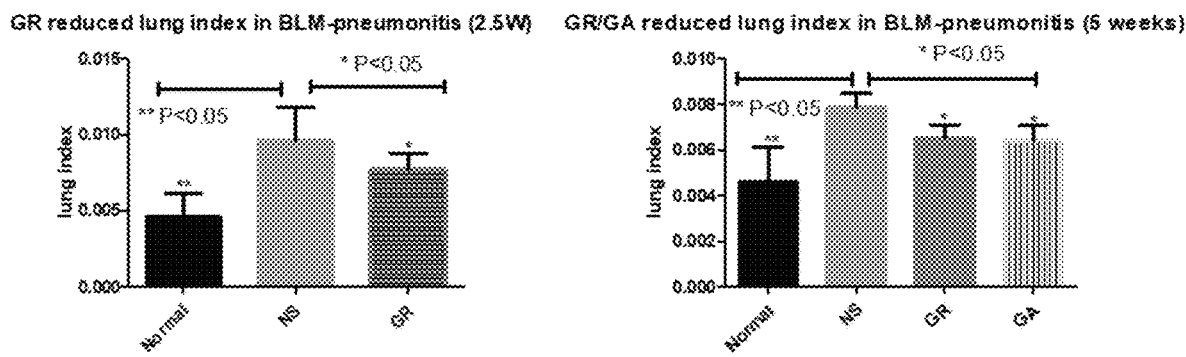
Figure 6G:
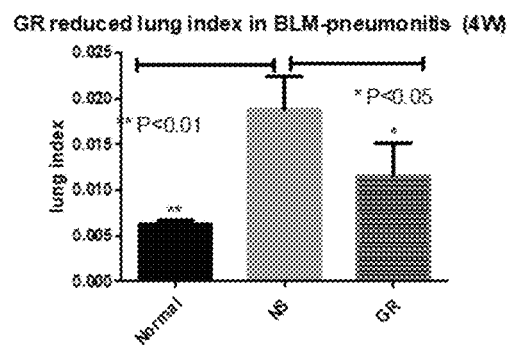
Figure 6H:
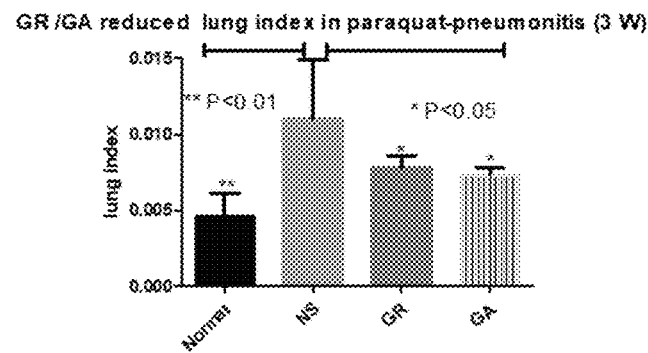
Figure 7A:
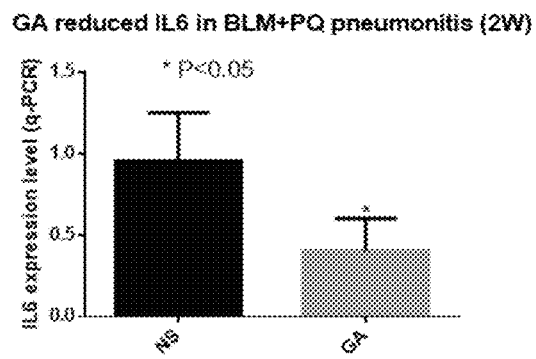
FIGS. 7A-7B show that GA reduces inflammatory mediators in bleomycin/paraquat-induced pneumonitis.
Figure 7B:
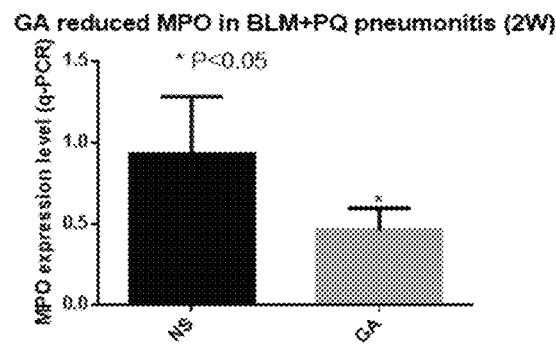
Figure 8A:
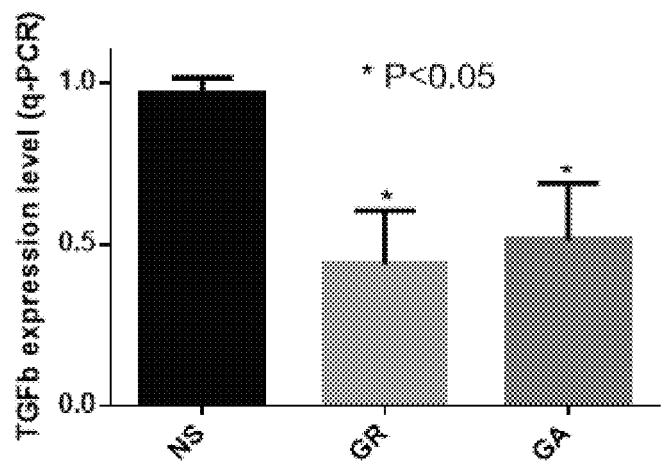
FIGS. 8A-8B show that GR/GA reduces fibrosis mediators in bleomycin-induced chronic lung damage.
Figure 8B:
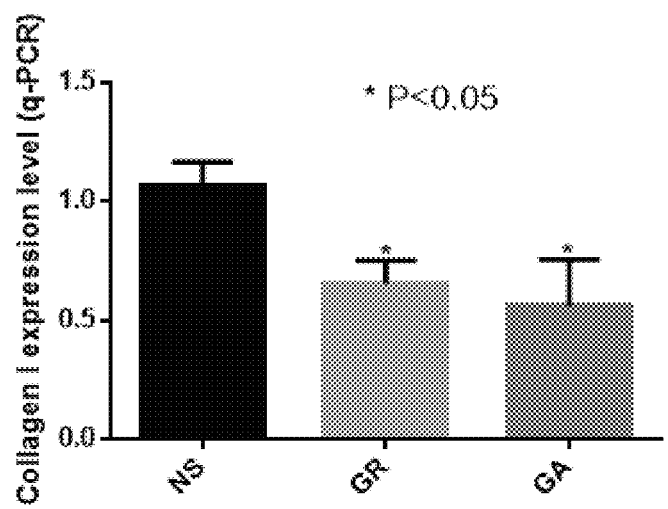

Dexamethasone did not prevent the loss of body weight, while GR and GA helped mice to maintain their body weight, indicating that unlike Dexamethasone, the GR and GA could prevent the physical decline due to the strong reaction of host to BLM-pneumonitis. The mitigation/treatment effect of GR and GA on the severity of BLM-pneumonitis is better than Dexamethasone in 3 week period (FIG. 4).

Example 6—GR/GA Reduces Lung Index in Various Chemicals-Induced Pneumonitis in ICR Mice ICR mouse was used as second strain mouse to test GR/GA effect on various chemical-induced pneumonitis. Mice inhaled different chemical solution in 100-130 ul volume. The chemicals included anti-cancer drugs, such as 5 mg/ml of Bleomycin (BLM), 1 mg/ml of Cisplatin, 5 mg/ml of 5-Fluorouracs (5-FU), 0.25 mg/ml of Mitomycin, 5 mg/ml of Methotrexate (MTX) and 0.1 mg/ml of paraquat.

These cytotoxic agents in the lung would cause pneumonitis, i.e., a stress response, releasing of inflammatory factors (MPO, IL 6 etc.), dilation of alveolar capillaries, increased permeability, plasma exudation, blood cells entering the lung interstitium/alveoli, resulting in an increased lung weight compared with body weight.

When mice were sacrificed at different time points, the whole lungs and mouse body were weighted. The lung index=lung wet weight/body weight. The normal lung index of ICR is 0.0043-0.0055.

The gavage of GR or GA significantly reduced the lung index, indicating that the GR and GA could alleviate the various chemicals-induced pneumonitis as evidenced in (FIG. 6 A-H).

Example 7—GA Reduces IL6 and MPO in Bleomycin+Paraquat-Induced Pneumonitis

ICR mice were inhaled with 130 ul of 5 mg/ml, and then 2 week later 0.1 mg/ml of paraquat with mitigation using GR or GA. After 2 weeks, mice were sacrificed and the lung tissue were examined with q-PCR for the expression of acute inflammation molecules, such as IL6 and MPO. GA reduces IL6 and MPO in Bleomycin+Paraquat-induced pneumonitis, indicating that GA could reduce the extent of chemically induced acute lung inflammation.

Example 8—GR/GA Reduces TGFβ and Collagen I in Bleomycin-Induced Late Lung Damage Mice were inhaled with 130 ul of 5 mg/ml of and 0.1 mg/ml of paraquat, 5 weeks later, mice were sacrificed and the lung tissue were examined with q-PCR for the expression of pro-fibrosis molecules, such as TGF and Collagen I. GR/GA reduced TGFb and Collagen I in BLM-induced pneumonitis, indicating that GA could reduce the extent of chemically induced lung damage towards fibrosis.

Example 9—GR/GA Reduces WBC in Various Chemicals-Induced Pneumonitis

To determine the effect of anti-inflammation agent, the blood is the most accessible sample. Therefore, we focused on testing blood samples. White blood cells (WBC) is the first-line immune cells of host against various chemical or biological invaders, which quickly surge to a high level. The increased WBC number is a good indicator for extent of inflammation. The higher WBC is, the severer pneumonitis exits.

Figure 9G:
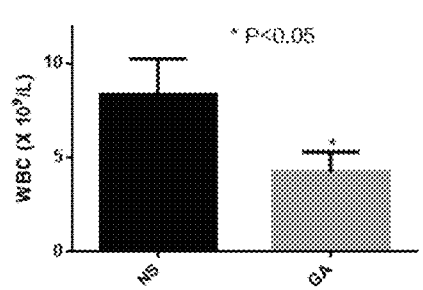
Figure 9H:
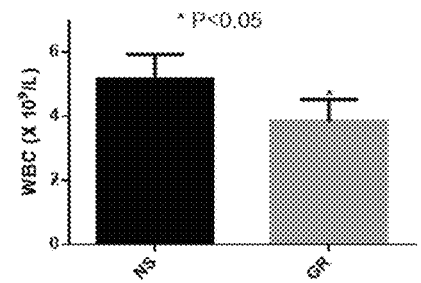

ICR mice were inhaled with different chemicals in 100-130 ul volume, such as anti-cancer drugs (5 mg/ml of Bleomycin, 1 mg/ml of Cisplatin, 5 mg/ml of 5-Fluorouracil, 0.25 mg/ml of Mitomycin, 5 mg/ml of Methotrexate) or 0.1 mg/ml of paraquat. Then, within one hour, mice were gavaged with 122 mg/kg/day of GR or 67 mg/kg/day of GA. At different time points, the mice were sacrificed and the blood were examined for WBC number. The results (FIG. 9 A-G) showed that GR/GA reduced WBC number in various chemicals-induced pneumonitis, suggesting that GR/GA alleviate the severity of various chemical-induced pneumonitis at different stages.

Figure 10A:
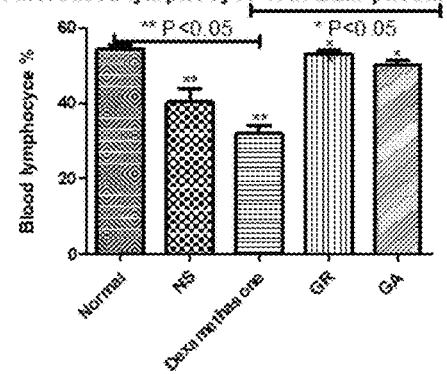
FIGS. 10A-10D show that GR/GA increase the percentage of blood lymphocytes in various chemicals-induced pneumonitis/pulmonary fibrosis, indicating the effect of GR/GA on enhancing host immunity.
Figure 10B:
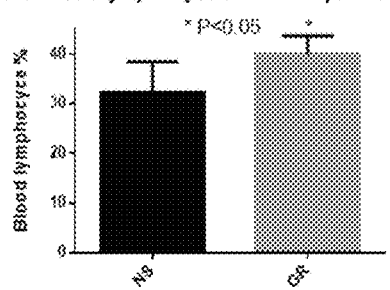
Figure 10C:
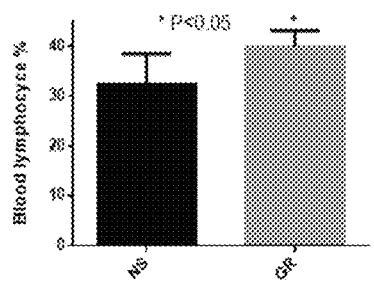
Figure 10D:
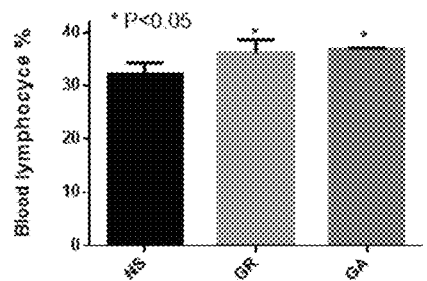

Example 10—GR/GA Increases Lymphocytes % in Various Chemicals-Induced Pneumonitis Lymphocytes, constituting 20-40% WBC, are the major player of host immunity. The increased lymphocytes % represents a strongly activated protective response and a good sign of recovery from inflammation or infection. GR/GA acted like a positive regulator for immune system and increased lymphocytes % in C57BL/5 mice (FIG. 10A) and ICR mice (FIG. 10 B-D) with various chemicals-induced pneumonitis, including anti-cancer drug 5-FU, BLM and Cisplatin. Although GR/GA have structure similar to Dexamethasone, a mostly used anti-inflammation drug, they acted differently. As showed in FIG. 10A, while the lymphocytes % of mice with BLM-pneumonitis treated with saline reduced greatly, the mice treated with Dexamethasone had a further reduced lymphocytes %, which were increased almost to the normal level in mice treated with GR/GA. This positive immune regulation might count for the reduced lung index and increased body weight, good signs for better prognosis.

Example 11—GR/GA Increases Number of Lymphocytes in BLM-Pneumonitis

It is well-recognized that the increased number of lymphocytes will reduce the NLR (Neutrophil-to-Lymphocyte Ratio) and has a good prognosis of inflammation or infection. While the C57BL/6 mice with BLM-pneumonitis were treated with Dexamethasone had a further reduced lymphocytes compared with saline-treated mice, GR/GA treated mice had an increased number of lymphocytes, a complete different action from Dexamethasone. GR/GA acted as positive immune regulator, leading to a better recovery from pneumonitis.

Example 12—GR/GA Reduces Neutrophils % in Various Chemicals-Induced Pneumonitis

The neutrophils constitute 50-70% of WBC. Clinically, an increased neutrophils % is regarded as host suffering from inflammation or infection. The higher neutrophils % is, the worst inflammation or infection would be.

Figure 11A:
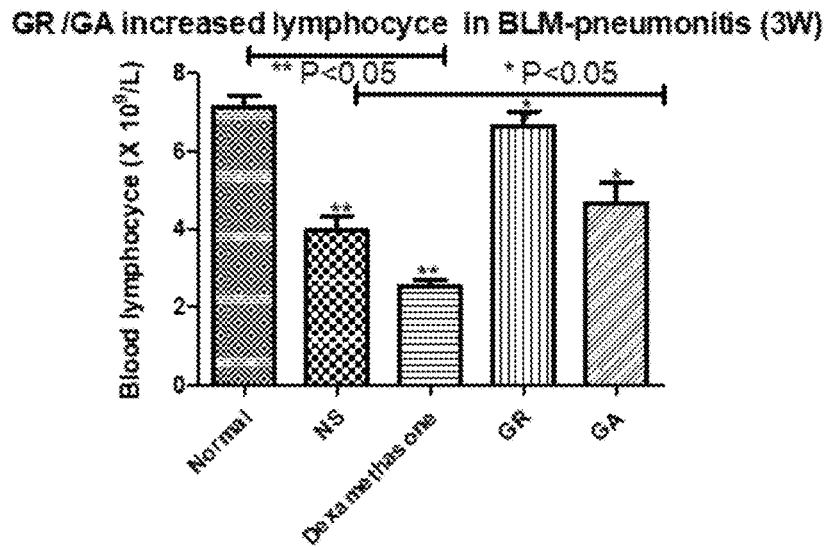
FIGS. 11A-11B show that GR/GA increases number of lymphocytes (enhancing host immunity) in BLM-pneumonitis, differently from dexamethasone which reduces the number of lymphocyte greatly.
Figure 11B:
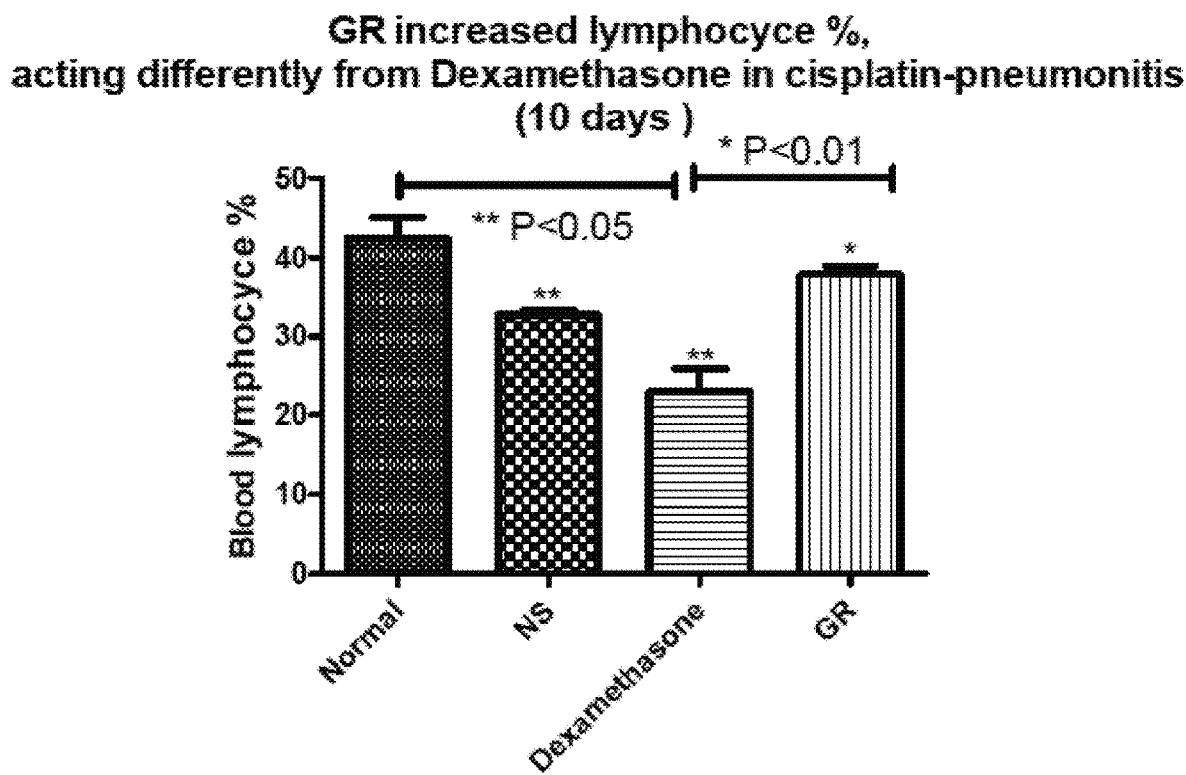
Figure 12A:
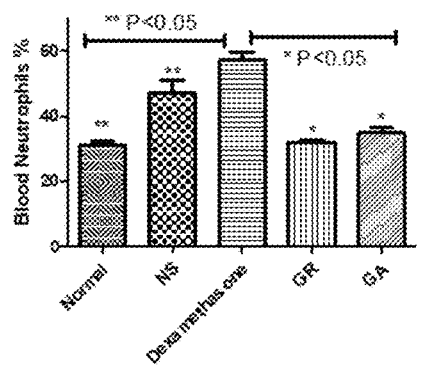
FIGS. 12A-12D show that that GR/GA reduces the percentage of blood neutrophils in various chemicals-induced pneumonitis/pulmonary fibrosis, indicating a systemic effect of GR/GA on anti-inflammation.
Figure 12B:
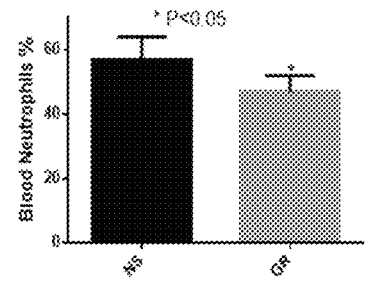
Figure 12C:
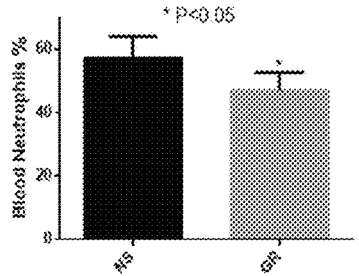
Figure 12D:
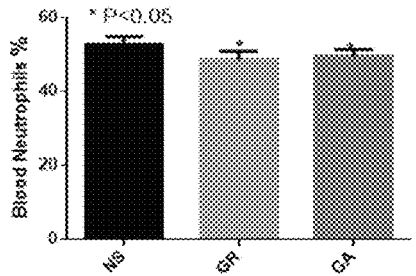
Figure 13A:
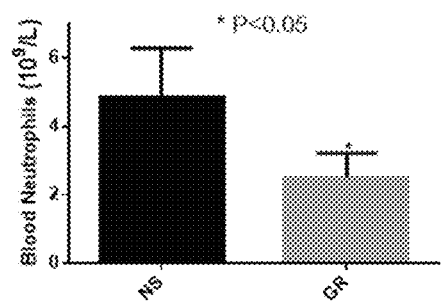
Figure 13B:
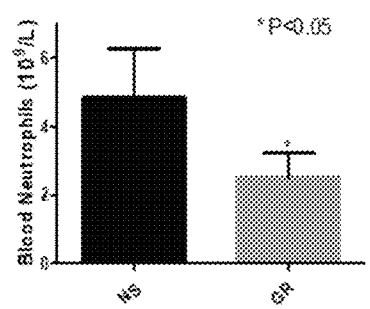

Fig A showed that the C57BL/6 mice with BLM-pneumonitis had a significantly increased neutrophils %, which was further increased in Dexamethasone-treated group. Acting differently from Dexamethasone, GR/GA greatly reduced the increased neutrophils %. Similar reduction effects were reproduced in ICR mice with various chemicals-induced pneumonitis (FIG. 11 B-D).

Example 13—GR/GA Reduces Number of Neutrophils in Various Chemicals-Induced Pneumonitis Like neutrophils %, an increased number of neutrophils indicates a severe inflammation or infection. The high NLR (Neutrophil-to-Lymphocyte Ratio) is an indicator for poor prognosis. GR/GA reduced the increased neutrophils in mice with pneumonitis induced by anticancer agents, inhibiting the over-reaction of host.

Example 14—GA Reduces the Growth of Tumor

To determine if GR/GA are used for mitigation/treatment of anti-cancer drugs induced pneumonitis has any blocking effect on anticancer, the GA (40 mg/kg) was used in ICR mice bearing with aggressive H22 liver cancer. The result indicated that GA could reduce the growth of cancer in vivo, suggesting that GA is safe to use with other anticancer drug.

Example 15—GA Reduces the Growth of Tumor in the Tumor Bearing Mice Treated with Active Immunotherapy Currently, the anticancer immunotherapy (such as anti-PD-1/PD-L1) and various small molecules targeting on Onco-pathway as well as tumor-vaccine have been widely used. The Drug-induced pneumonitis is one of severe side effect.

To determine if GA affects the anti-cancer immunotherapy, the H22 tumor-bearing mice were immunized with H22 vaccine, and GA (40 mg/kg) was used for anti-inflammation. The traditional Aspirin (60 mg/kg) was used as drug-control. The results showed that the H22 vaccine reduced tumor volume (A) and slow-down the tumor growth in the followed-up observation (B), which was not affected when combination use of GA, suggesting that GA could be safely used with anti-cancer immunotherapy to reduce the drug-induced pneumonitis and enhance the anti-cancer effect.

Example 16—GA Prolongs the Survival of Tumor Bearing Mice Treated with Active Immunotherapy Survival rate is the strong evidence to prove that the drug has positive effect without toxicity. The survival result of 80 day followed up in mice bearing 1422 tumor treated with H22 vaccine and GA showed that GA could prolong the survival time of mice, suggesting that GA as immune regulator and anti-inflammation agent is of benefit for anti-cancer immunotherapy while reducing drug-induced pneumonitis.

Example 17—GR Reduces Osimertinib-Induced Pneumonitis in Patient with Lung Cancer The anti-cancer immunotherapy (such as anti-PD-1/PD-L1) and various small molecules targeting on Onco-pathway could cause drug-induced interstitial pneumonitis.

A patient with lung cancer was treated with Osimertinib (80 mg/day), targeting EGFR pathway. One month later, mild pneumonitis occurred (FIG. 17A) and became severer in two months (FIG. 17 B). At this time point, GR (300 mg/day) was orally used and the extent of Osimertinib-pneumonitis was reduced after one month use of GR (FIG. 17 C). Six months after using GR, pneumonitis subsided while Osimertinib was continuously used to target EGFR pathway (FIG. 17 D). Data suggest that since GR/GA have the potential against pneumonitis induced by anti-cancer drugs, it is worthy to carry out clinical trial to explore the appropriate dose and treatment schedule.

Example 18—GR/GA Reduces Lung Index and Spleen Index as Well as WBC in H1N1-Pneumonia Pathogens, such as virus, cause pneumonia, especially COVID-19, affecting billions life and causing death of millions worldwide. Drugs against virus-pneumonia are urgently needed.

GR/GA possess good characteristics of high therapeutic window ($ED_{50}/LD_{50}$>400-1000), effective, easy to use orally, low cost, stable with years of shelf-life and easy to produce in a large quantity. Therefore, we tested the effect GR/GA on H1N1-flu model since lack of safety condition to perform the testing in COVID-19 animal model.

The viral strain of H1N1 A/FM/1/47 was used to infect mice and observed at two time points: 1 week (7 days) and 12 days. The virus was tittered to $2 \times LD_{50}$ for groups of 7 days and $1 \times LD_{50}$ for 12 days.

C57BL/6 mice (~18 g, male) were anesthetized with isoflurane, then 30 ul of viral solution was pipetted into the mouse's nostril (15 ul each side) and waiting for the mouse to inhale completely. The mice were divided into four groups: 1) Normal: receiving 1640 medium vehicle without virus; 2) NS: viral infected and treated with saline as vehicle control; 3) Ribavirin: viral infected and treated with Ribavirin for anti-virus; 4) GR: viral infected and treated with 70 mg/kg of GR.

Figure 18A:
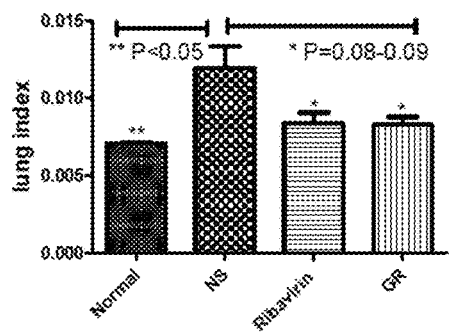
FIGS. 18A-18D show that GR/GA reduces lung index and spleen index as well as WBC in mice H1N1-pneumonia, acting differently from Ribavirin.
Figure 18B:
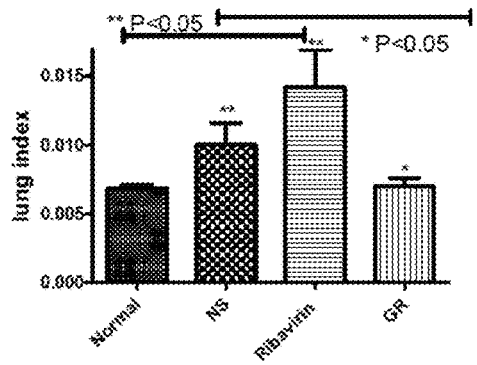
Figure 18C:
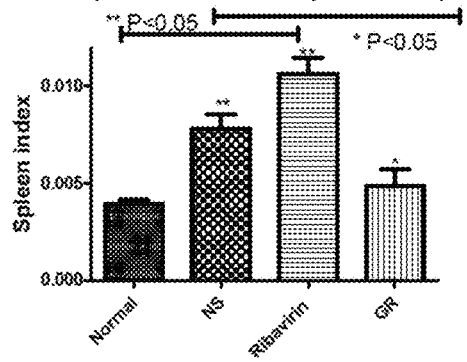
Figure 18D:
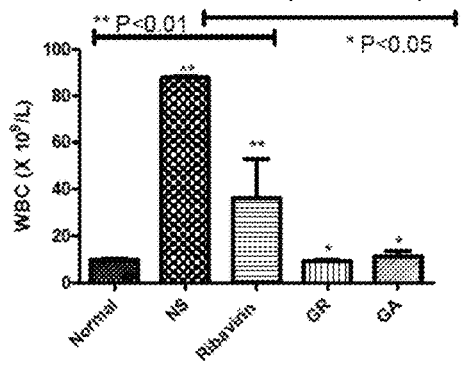

After 2 hours of nasal drip, the mice were completely awakened, and were given the agents by gavage, followed by once a day. The weight of mice was recorded every 2 days. After the 7 days or 12 days of viral infection, the mice were sacrificed, the bodies were weighted, the weights of lung and spleen were measured, and the blood were tested for hemogram. The results showed that: 1) GR acted like Ribavirin to reduce the lung index at day 7 (FIG. 18A), suggesting that GR suppressed the virus-pneumonia. For unknown reason, on day 12, the lung index of Ribavirin treated mice was surged higher than NS control, while the GR treated mice still had a reduced lung index (FIG. 18B), indicating that GR acted differently from Ribavirin as prolong of treatment; 2) On day 12, GR group had a reduced spleen index compared to groups of NS and Ribavirin, closed to normal mice, indicating that the strong acute immune response of host to viral infection was gradually vanished by GR (FIG. 18C), but not by Ribavirin; 3) On day 12, while the WBC number in NS group was in a significantly high level compared to that in normal mice, the GR and GA group had a reduced WBC number greater than Ribavirin (FIG. 18D), suggesting that GR and GA could strongly inhibit the viral inflammation.

Figure 19A:
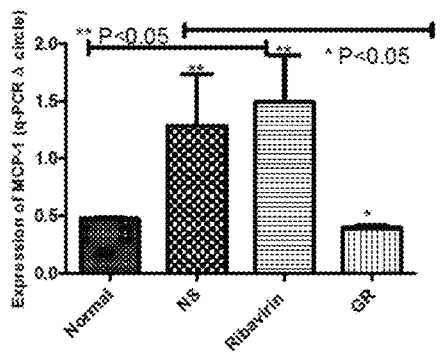
FIGS. 19A-19D show that GR reduces MCP-1/IFNr and increases lymphocytes %, acting differently from Ribavirin in H1N1-pneumonia.
Figure 19C:
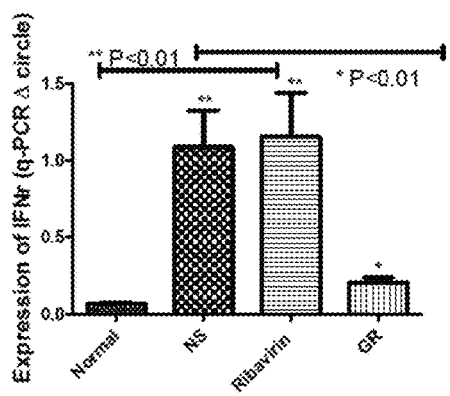
Figure 19B:
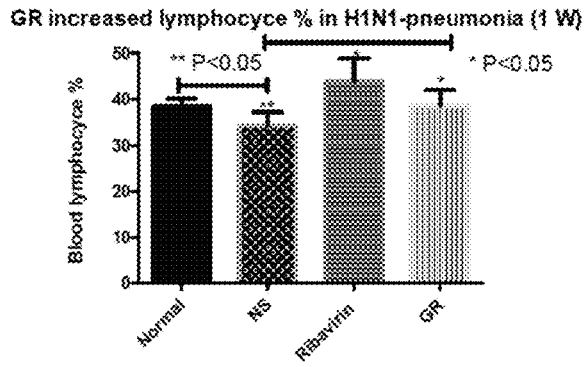
Figure 19D:
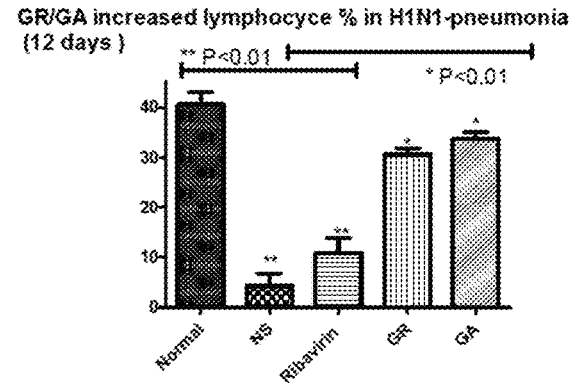
Figure 20A:
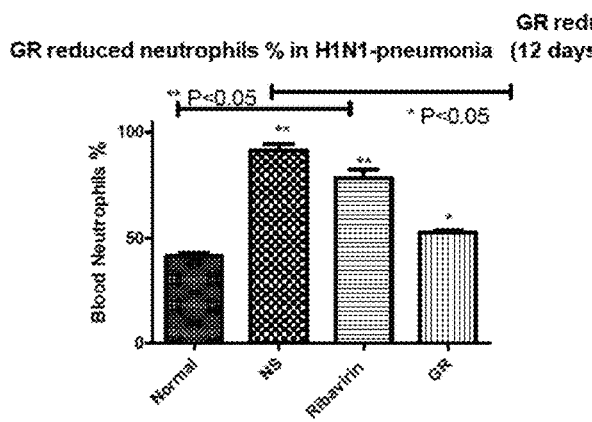
FIGS. 20A-20D show that GR reduces neutrophils % and number and increase lymphocyte number, thereby reducing the NLR in H1N1-pneumonia, a good sign for host immunity and outcome.
Figure 20B:
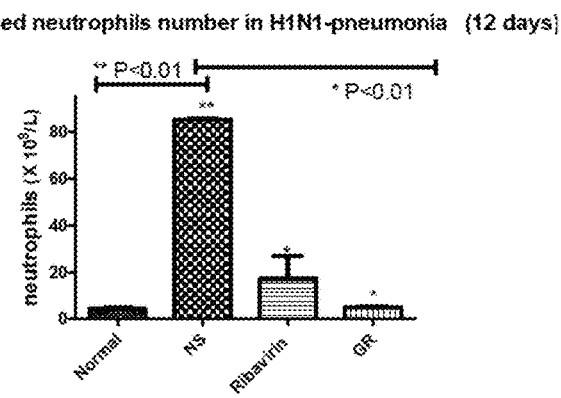
Figure 20C:
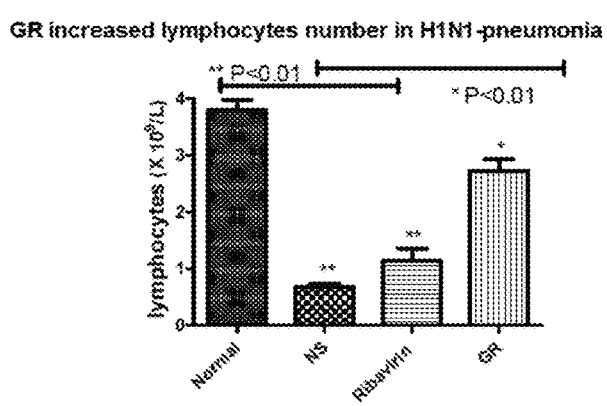
Figure 20D:
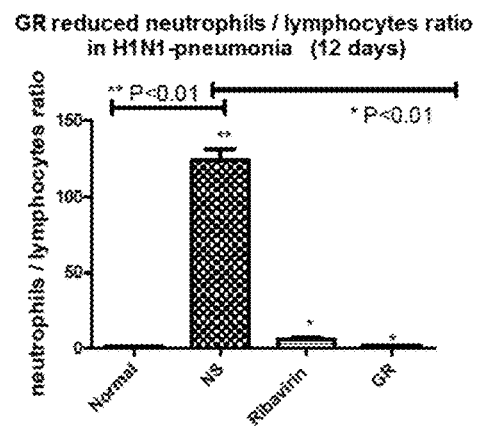

Example 19—GR Reduces MCP-1/IFNg and Increases Lymphocytes %, Acting Differently from Ribavirin in H1N1-Pneumonia On molecular level, on day 12, NS and Ribavirin had a high level of MCP-1 or IFNg, while GR reduces MCP-1 to a normal level and IFNg much less than that in NS and Ribavirin group (FIGS. 19 A and B), indicating a reduced viral inflammation response in GR-mice, but not in Ribavirin-mice. Regarding lymphocytes %, a sign for host immunity, while virus reduced it on day 7 of infection, the Ribavirin and GR slightly increased it (FIG. 19C). However, on day 12, lymphocytes % dropped dramatically in NS and Ribavirin treated mice, while it was significantly increased by GR/GA (FIG. 19D), indicating that GR/GA acted differently from Ribavirin in H1N1-pneumonia to enhance the host anti-virus immunity.

Example 20—GR Reduces Neutrophils % and Number and Increases Lymphocytes Number, Reduces NLR in H1N1-Pneumonia The neutrophils % and number are the indicators for infection, while they were dramatically increased in NS group, the GR reduced them in greater degree than Ribavirin (FIGS. 20 A and B). On the other hand, while the lymphocytes number was dramatically reduced in NS group, GR increased it in greater degree than Ribavirin (FIG. 20 C). As a result, the ratio of neutrophils to lymphocytes (NLR), a clinically important index, increased by H1N1 on day 12 was reduced by GR and Ribavirin (FIG. 20 D), indicating that GR acts as immune regulator, which might contribute to its effect on anti-virus-pneumonia.

Example 21—New Processes for Alteration Analysis of CT Density Before and after Treatments of Lung Damage Lung CT, non-invasive mean, is the best to define the changes of lung, especially the small change that could not be defined by human eye. CT is the best tool to determine if the drug could reduce the severity of pneumonia/pneumonitis, since the clinical symptoms (such as cough, shortness of breath, chest tightness, weakness, fever, etc.) are difficult to be quantitative and appear much later than CT abnormality.

To determine the drug effects, the CT must be taken before and after using drug. To ensure the lung alterations can be precisely defined using serial CTs, the CT imaging with similar anatomic position is critical, which must be done by tight control of the consistents in 1) the body position of patient, 2) CT imaging parameters of device, and 3) the same operator.

Figure 21A:
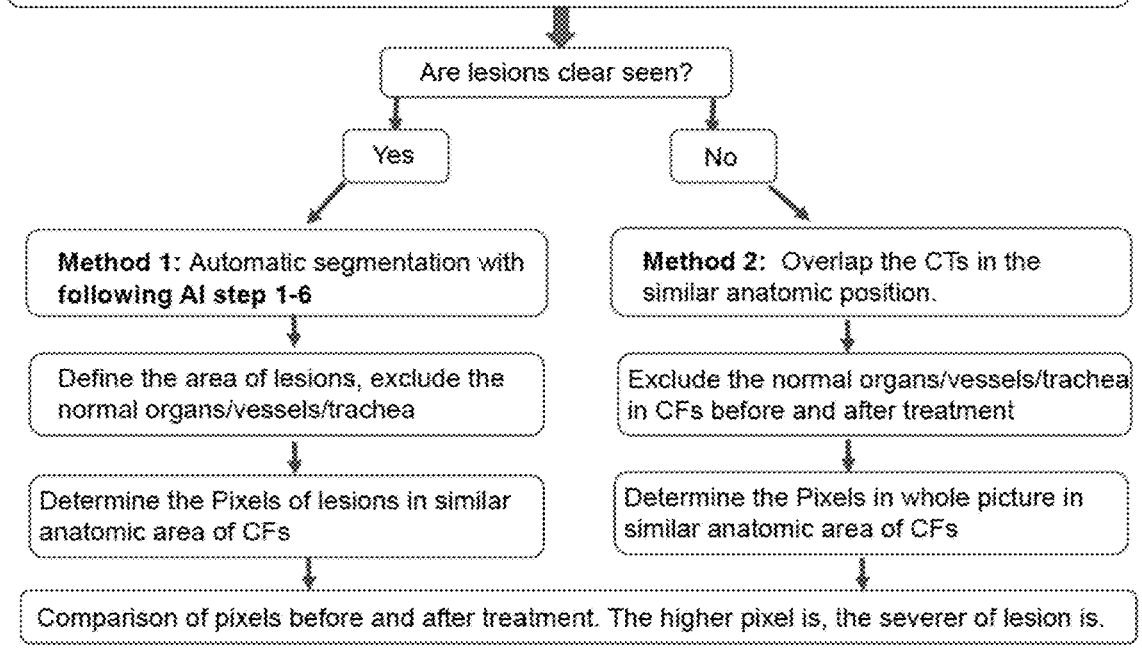
Figure 21B:
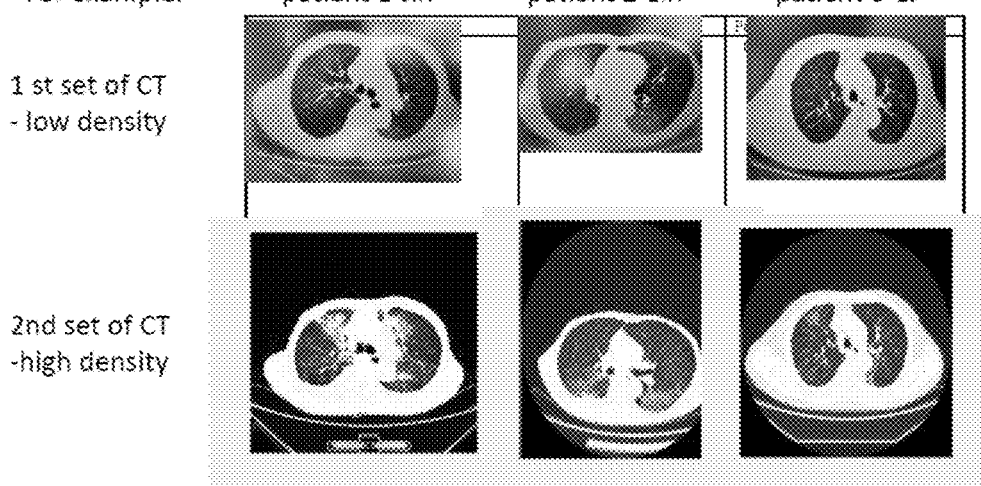
Figure 21E:
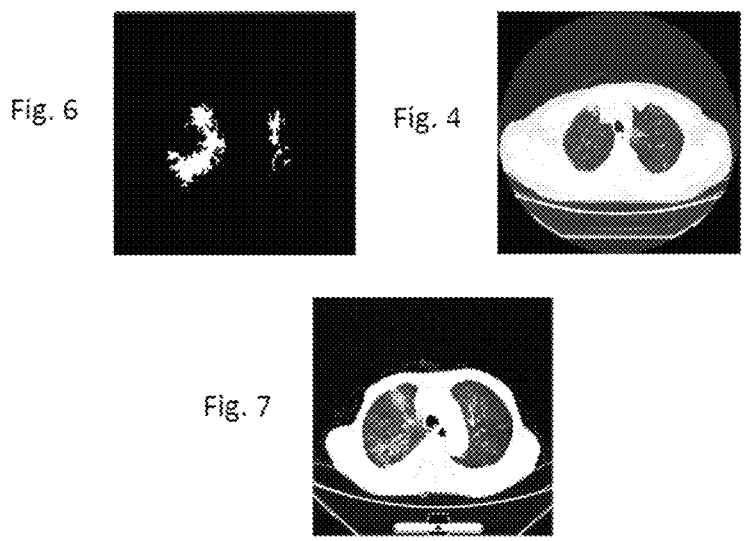

As shown in FIG. 21A, the processes for alteration analysis of CT density (determined with pixel) before and after treatments of lung damage depend on 1) lung lesion, if clear, method 1 can be used for automatic segmentation analysis of alterations of CT density with lesion; 2) CTs have a very similar anatomic position, after the normal organs/vessels/trachea have been defined and excluded, the pixels in whole CT with similar anatomic area can be measured and compared to determine the alteration of lung density before and after treatment.

The automatic segmentation analysis for lung lesion has 6 steps as demonstrated in FIG. 21B-E.

Figure 21F:
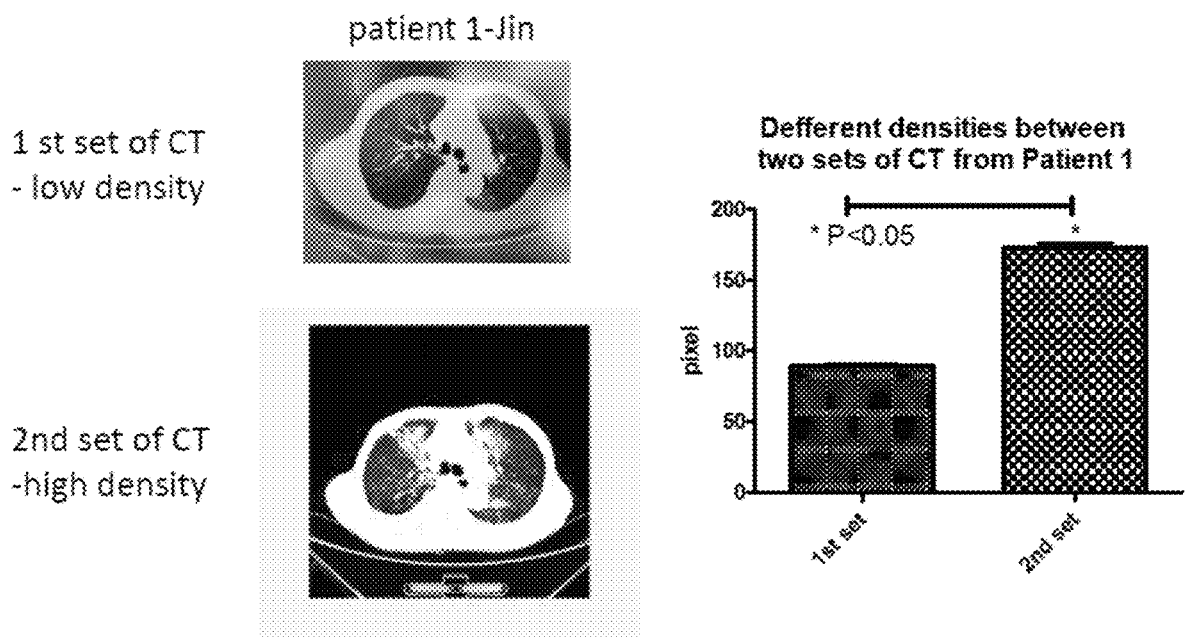
Figure 21G:
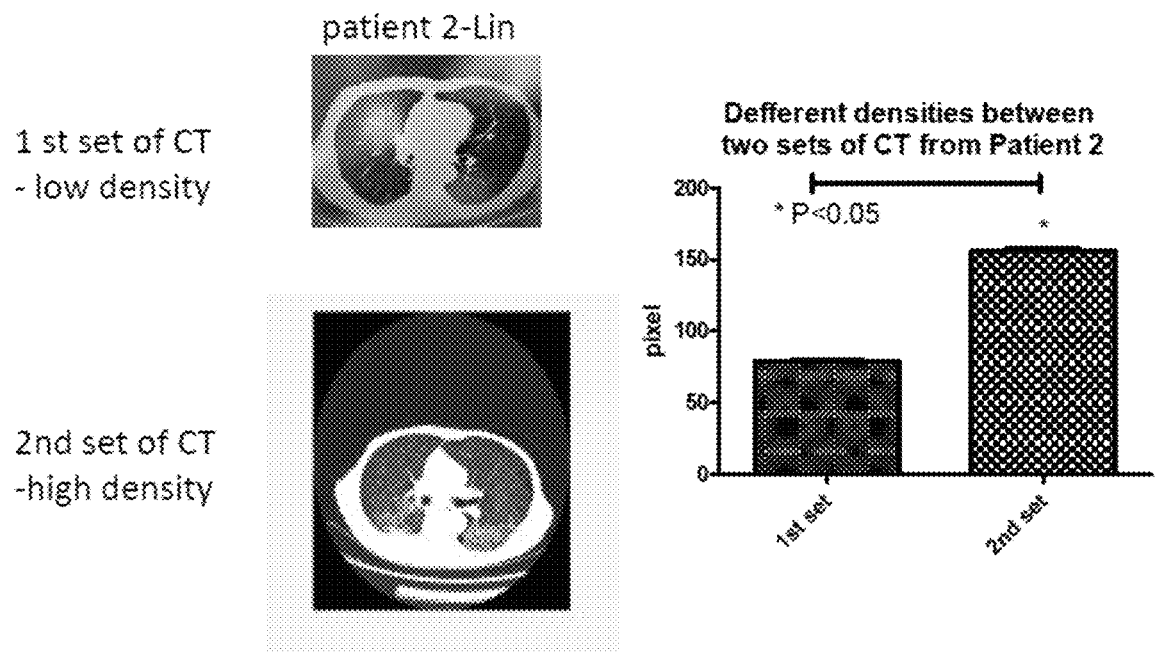
Figure 21H:
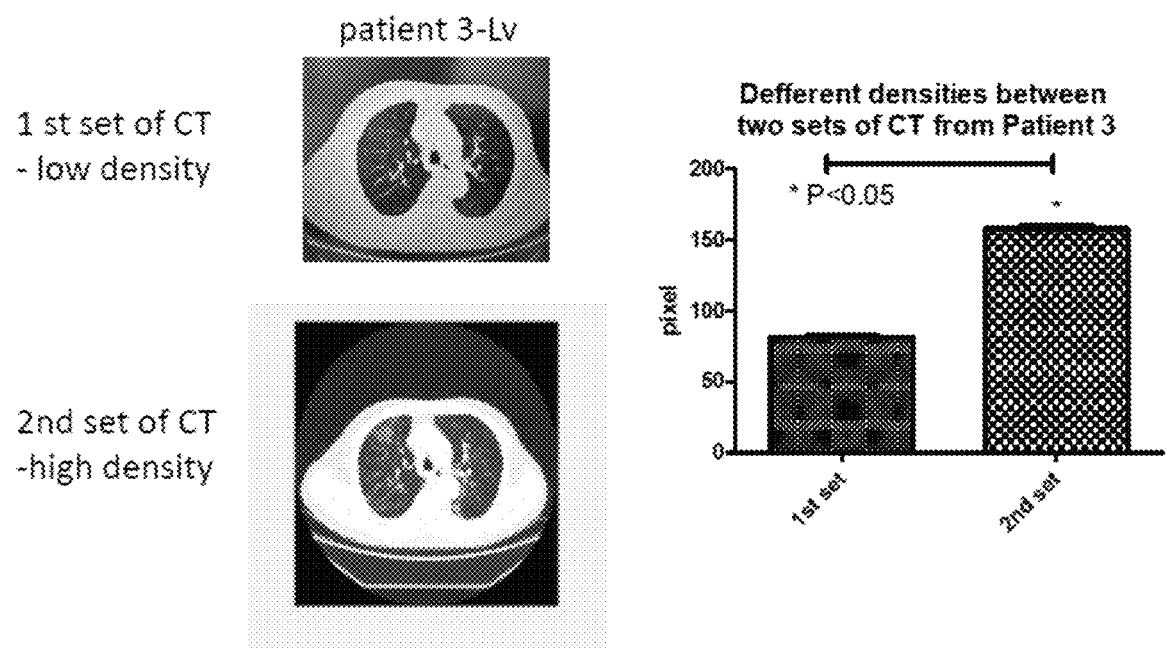

FIG. 21F-H show the pixel density altered in serial CTs of three patients defined by our new assessment method.

Example 22—New Findings of Differences in Pharmacokinetics (PK) Between GR and GA As shown in FIG. 1, GR is a glucoside and water soluble. After oral taken, it is converted into GA, an aglycone, fat soluble and easily absorbed through double lipid layer. Therefore, we propose that their pharmacokinetics (PK) should be different. To prove this, ICR mice (8 weeks) were weighted and divided into GR or GA groups (5 mice/group), and orally given 400 mg/kg of GR or 224 mg/kg of GA (equal mole used for comparison), then the blood was taken from mouse at time points of 0.25, 0.5, 1.5, 2, 3, 4, 6, 8, 12, 24, 48 hours after gavage of GR or GA. 100 µl of plasma was added with 30 μl internal standard solution (100 ng/ml) and then 0.5 ml ethyl acetate. The mixture was vortex mixed for 3 min, centrifuged at 14 000×g for 15 min, and then removed 470 μl of supernatant to dry. After re-dissolved in 100 μl of acetonitrile-water (80☐20, V/V, mobile phase agent), 20 μl was used for LC-MS/MS analysis.

As we expected, we revealed for the first time using equal mole use and side-by-side comparison that the GA absorption is much faster (Tmax GA 0.5 hr vs GR 12 hr) and at a higher level (Cmax GA 49096 vs GR 10842) as shown in FIG. 22 and FIG. 23.

The PK difference will be taken into consideration when both GR and GA are developing into drugs.

It should be understood that the examples and embodiments described herein are for illustrative purposes only and that various modifications or changes in light thereof will be suggested to persons skilled in the art and are to be included within the spirit and purview of this application and the scope of the appended claims.

All references, including publications, patent applications and patents, cited herein are hereby incorporated by reference to the same extent as if each reference was individually and specifically indicated to be incorporated by reference and was set forth in its entirety herein.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

What is claimed:

1. A method of treating or mitigating acute or sub-acute pneumonia or pneumonitis induced by at least a targeted anti-cancer drug, a chemical toxin, a virus, and/or a bacterial toxin, wherein said method comprises administering, to a subject in need of such treatment or mitigation, an effective amount of an isolated compound or a salt thereof, wherein said compound is selected from the group consisting of:
(A) glycyrrhetinic acid (GA);
(B) glycyrrhizic acid (GLA);
(C) ester, ether and/or amide forms of glycyrrhetinic acid (GA), represented by the following structure (Structure C):

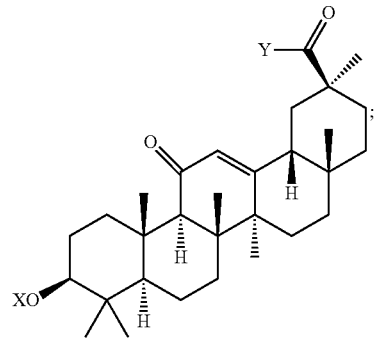

and
(D) ester and/or amide forms of glycyrrhizic acid (GLA), represented by the following structure (Structure D):

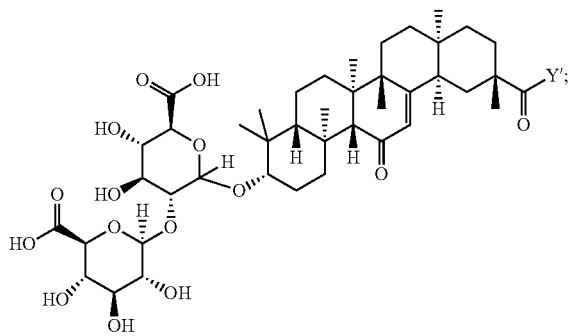

wherein
X is selected from the group consisting of
a) alkyl, substituted alkyl, alkenyl, substituted alkenyl, acyl, alkylcarbonyl, benzyl, cyclic alkyl, and cyclic alkenyl;
b) an acid group selected from the group consisting of acetic acid, carboxylic acid, aspartic acid, formic acid, citric acid, benzoic acid, hippuric acid, malic acid, mucic acid, phosphoric acid, sulfuric acid, gluconic acid, maleic acid, succinic acid, tartaric acid, and lactic acid; and
c) a carbohydrate moiety; and
each of Y and Y' is —$NH_2$, alkylamino, or alkoxy,
wherein said subject has been diagnosed to have said acute or sub-acute pneumonitis induced by at least a targeted anti-cancer drug, a chemical toxin, a virus, and/or a bacterial toxin, and wherein said targeted anti-cancer drug comprises osimertinib, cisplatin, 5-fluorouracil, and/or mitomycin.

2. The method, according to claim 1, wherein the subject is a human.

3. The method, according to claim 1, wherein the compound is glycyrrhetinic acid (GA) or a salt thereof.

4. The method, according to claim 1, wherein the compound is glycyrrhizic acid (GLA) or a salt thereof.

5. The method, according to claim 1, wherein said acute or sub-acute pneumonitis has been induced by at least a chemical toxin which is paraquat.

6. The method, according to claim 5, wherein said acute or sub-acute pneumonitis has also been induced by bleomycin.

7. The method, according to claim 1, wherein the subject has been diagnosed with said acute or sub-acute pneumonitis induced by a virus which is COVID-19 pneumonia or H1N1-pneumonia.

8. The method, according to claim 1, comprising administering, to the subject, glycyrrhizic acid or a salt thereof an oral dose of 150-600 mg per day, or administering, to the subject glycyrrhetinic acid or a compound with a glycyrrhizin functional group, or a salt thereof, an oral dose of 100-400 mg per day.

9. The method, according to claim 8, wherein said glycyrrhizic acid or a salt thereof or said compound with a glycyrrhizin functional group, or a salt thereof, is administered as a form of drug, health product, food or food additive.

* * * * *